US012808864B2

(12) United States Patent
Liu et al.

(10) Patent No.: US 12,808,864 B2
(45) Date of Patent: Nov. 24, 2026

(54) POINT-OF-CARE DIGITAL MICROFLUIDICS FOR SEPSIS DIAGNOSIS

(71) Applicant: Mayo Foundation for Medical Education and Research, Rochester, MN (US)

(72) Inventors: Yuguang Liu, Rochester, MN (US); Marina R. Walther-Antonio, Rochester, MN (US); Nicholas Chia, Rochester, MN (US); Heidi Nelson, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 925 days.

(21) Appl. No.: 17/912,713

(22) PCT Filed: Mar. 19, 2021

(86) PCT No.: PCT/US2021/023123
§ 371 (c)(1),
(2) Date: Sep. 19, 2022

(87) PCT Pub. No.: WO2021/188877
PCT Pub. Date: Sep. 23, 2021

(65) Prior Publication Data

US 2023/0133186 A1 May 4, 2023

Related U.S. Application Data

(60) Provisional application No. 62/992,061, filed on Mar. 19, 2020.

(51) Int. Cl.

| | |
|---|---|
| ***G01N 33/543*** | (2006.01) |
| ***B01L 3/00*** | (2006.01) |
| ***G01N 33/569*** | (2006.01) |

(52) U.S. Cl.
CPC .. *G01N 33/54366* (2013.01); *B01L 3/502792* (2013.01); *G01N 33/56966* (2013.01); *B01L 2300/0816* (2013.01)

(58) Field of Classification Search
CPC ....... G01N 33/56966; G01N 33/54366; G01N 2333/70589; B01L 3/502792; B01L 3/502761; B01L 2300/0867
See application file for complete search history.

(56) References Cited

U.S. PATENT DOCUMENTS

| | | | |
|---|---|---|---|
| 2013/0225452 A1 | 8/2013 | Pollack et al. | |
| 2014/0370519 A1 | 12/2014 | Vangbo et al. | |

(Continued)

FOREIGN PATENT DOCUMENTS

| | | |
|---|---|---|
| AU | 2010212376 | 9/2010 |
| JP | 5882234 | 3/2016 |
| WO | WO 2017/205304 | 11/2017 |

OTHER PUBLICATIONS

Kim et al. (A Microfluidic DNA Library Preparation Platform for Next-Generation Sequencing. PLoS One 8 (7): e68988 (Jul. 22, 2013).*

(Continued)

*Primary Examiner* — Gailene Gabel
(74) *Attorney, Agent, or Firm* — Fish & Richardson P.C.

(57) ABSTRACT

This document provides digital microfluidics devices. For example, point-of-care digital microfluidics devices for removing white blood cells from a blood sample and preparing bacterial DNA in the sample for detection and/or identification are provided.

9 Claims, 19 Drawing Sheets

(56) References Cited

U.S. PATENT DOCUMENTS

| | | | |
|---|---|---|---|
| 2015/0260711 A1 | 9/2015 | Toner et al. | |
| 2018/0169660 A1* | 6/2018 | Tan | G01N 27/44726 |
| 2018/0230512 A1 | 8/2018 | Hansen et al. | |
| 2018/0353913 A1 | 12/2018 | Link et al. | |
| 2020/0166509 A1* | 5/2020 | Chia | G01N 15/1023 |
| 2023/0219091 A1* | 7/2023 | Jebrail | B01L 3/502792 506/26 |

OTHER PUBLICATIONS

Balloux et al., "From Theory to Practice: Translating Whole-Genome Sequencing (WGS) into the Clinic," Trends in Microbiology, 26(12):1035-1048, Sep. 4, 2018.
Binga et al., "Something from (almost) nothing: the impact of multiple displacement amplification on microbial ecology," ISME Journal, 2(3):233-241, Feb. 7, 2008.
Bushnell et al., "BBMerge—Accurate paired shotgun read merging via overlap," PLoS One, 12(10):e0185056, Oct. 26, 2017, 15 pages.
Chang et al., "Low voltage electrowetting on atomic-layer-deposited aluminum oxide," Presented at Proceedings of the 2010 IEEE 5th International Conference on Nano/Micro Engineered and Molecular Systems, Xiamen, China, Jan. 20-23, 2010, 5 pages.
Chapela et al., "Detection of foodborne pathogens by qPCR: a practical approach for food industry applications," Cogent Food and Agriculture, 1(1):1013771, Mar. 5, 2015, 20 pages.
ChemistryWorld.com [online], "Human genome sequenced by hand-held device," Feb. 1, 2018, retrieved on Mar. 27, 2023, retrieved from URL<https://www.chemistryworld.com/news/human-genome-sequenced-by-handheld-device-/3008598.article>, 2 pages.
Chen et al., "Breast Cancer Subtype Classification Using 4-Plex Droplet Digital PCR," Clin. Chemistry, 65(8):1051-1059, Apr. 22, 2019.
Chen et al., "Comparison of Multiple Displacement Amplification (MDA) and Multiple Annealing and Looping-Based Amplification Cycles (MALBAC) in Single-Cell Sequencing," PLoS One, 9(12):e114520, Dec. 8, 2014, 12 pages.
Chen et al., "Dielectrophoretic Separation of Particles Using Microfluidic Chip with Composite Three-Dimensional Electrode," Micromachines, 11(7):700, Jul. 20, 2020, 15 pages.
Chen et al., "Single-cell whole-genome analyses by Linear Amplification via Transposon Insertion (LIANTI)," Science, 356(6334):189-194, Apr. 14, 2017.
Cho et al., "Creating, transporting, cutting, and merging liquid droplets by electrowetting-based actuation for digital microfluidic circuits," J. Microelectromech. Systems, 12(1):70-80, Feb. 28, 2003.
Choi et al., "Digital microfluidics," Ann. Rev. Anal. Chemistry, 5:413-440, Apr. 9, 2012.
De Bourcy et al., "A quantitative comparison of single-cell whole genome amplification methods," PLoS One, 9(8):e105585, Aug. 19, 2014, 9 pages.
Dean et al., "Rapid amplification of plasmid and phage DNA using Phi 29 DNA polymerase and multiply-primed rolling circle amplification," Genome Research, 11(6):1095-1099, Jun. 2001.
Deshmukh et al., "Recent developments in detection and enumeration of waterborne bacteria: a retrospective minireview," MicrobiologyOpen, 5(6):901-922, Jul. 10, 2016.
Deurenberg et al., "Application of next generation sequencing in clinical microbiology and infection prevention," J. Biotechnology, 243:16-24, Dec. 29, 2016.
Di Tommaso et al., "Nextflow enables reproducible computational workflows," Nat. Biotechnology, 35(4):316-319, Apr. 11, 2017.
Didelot et al., "Transforming clinical microbiology with bacterial genome sequencing," Nat. Rev. Genetics, 13(9):601-612, Aug. 7, 2012.
Edwards et al., "Real-time selective sequencing with RUBRIC: read until with basecall and reference-informed criteria," Sci. Reports, 9(1):11475, Aug. 7, 2019.
Fair, "Digital microfluidics: Is a true lab-on-a-chip possible?," Microfluid. Nanofluidics, 3(3):245-281, Apr. 2007.
Fobel et al., "DropBot: An open-source digital microfluidic control system with precise control of electrostatic driving force and instantaneous drop velocity measurement," Appl. Phys. Letters, 102(19):193513, May 17, 2013, 5 pages.
Fricke et al., "Bacterial genome sequencing in the clinic: bioinformatic challenges and solutions," Nat. Rev. Genetics, 15(1):49-55, Nov. 26, 2013.
Gawk et al., "Progress in Circulating Tumor Cell Research Using Microfluidic Devices," Micromachines, 9(7):353, Jul. 14, 2018, 21 pages.
Gorgannezhad et al., "Microfluidic-Based Nucleic Acid Amplification Systems in Microbiology," Micromachines, 10(6):408, Jun. 19, 2019.
Hammond et al., "Picodroplet partitioned whole genome amplification of low biomass samples preserves genomic diversity for metagenomic analysis," Microbiome, 4(1):52, Oct. 6, 2016.
Hochstetter et al., "Deterministic Lateral Displacement: Challenges and Perspectives," ACS Nano, 14(9):10784-10795, Aug. 26, 2020.
International Preliminary Report on Patentability in International Appln. No. PCT/US2021/023123, mailed on Sep. 29, 2022, 6 pages.
International Search Report and Written Opinion in International Appln. No. PCT/US2021/023123, mailed on Jun. 24, 2021, 8 pages.
Kim et al., "Centrifuge: rapid and sensitive classification of metagenomic sequences," Genome Research, 26(12):1721-1729, Oct. 17, 2016.
Kimura et al., "Utilization of a *Cyanobacterium, Nostoc* sp. HK-01, under the space environment," Presented at Proceedings of the 44th International Conference on Environmental Systems, Tucson, AZ, USA, Jul. 13-17, 2014, 6 pages.
Lan et al., "Single-cell genome sequencing at ultra-high-throughput with microfluidic droplet barcoding," Nat. Biotechnology, 35(7):640-646, May 29, 2017.
Landry et al., "Optofluidic cell selection from complex microbial communities for single-genome analysis," Methods in Enzymology, 531:61-90, 2013.
Law et al., "Rapid methods for the detection of foodborne bacterial pathogens: principles, applications, advantages and limitations," Front. Microbiology, 5:770, Jan. 12, 2015, 19 pages.
Lee et al., "An integrated microfluidic chip for one-step isolation of circulating tumor cells," Sens. Actuators B Chemical, 238:1144-1150, Jan. 2017.
Leipert et al., "Miniaturized sample preparation on a digital microfluidics device for sensitive bottom-up microproteomics of mammalian cells using magnetic beads and mass spectrometry-compatible surfactants," Lab Chip, 19(20):3490-3498, Sep. 2019.
Lewin et al., "Evolution and Ecology of Actinobacteria and Their Bioenergy Applications," Ann. Rev. Microbiology, 70:235-254, Sep. 8, 2016.
Li et al., "The Sequence Alignment/Map format and SAMtools," Bioinformatics, 25(16):2078-2079, Jun. 8, 2009.
Li, "Minimap2: pairwise alignment for nucleotide sequences," Bioinformatics, 34(18):3094-3100, Sep. 15, 2018.
Liu et al., "Amplification of Femtograms of Bacterial DNA Within 3 h Using a Digital Microfluidics Platform for MinION Sequencing," ACS Omega, 6(39):25642-25651, Sep. 23, 2021.
Liu et al., "Bacterial Single Cell Whole Transcriptome Amplification in Microfluidic Platform Shows Putative Gene Expression Heterogeneity," Anal. Chemistry, 91(13):8036-8044, Jun. 12, 2019.
Liu et al., "Heterogeneous Immunoassay Using Channels and Droplets in a Digital Microfluidic Platform," Micromachines, 10(2):107, Feb. 5, 2019, 12 pages.
Liu et al., "Microfluidics: A new tool for microbial single cell analyses in human microbiome studies," Biomicrofluidics, 11(6):061501, Nov. 2017.
Liu et al., "Precise droplet volume measurement and electrode-based vol. metering in digital microfluidics," Microfluid. Nanofluidics, 17:295-303, Jan. 10, 2014.
Liu et al., "The Development of an Effective Bacterial Single-Cell Lysis Method Suitable for Whole Genome Amplification in Microfluidic Platforms," Micromachines, 9(8):367, Jul. 25, 2018, 17 pages.
Liu et al., "Whole genome amplification of single epithelial cells dissociated from snap-frozen tissue samples in microfluidic platform," Biomicrofluidics, 13(3):034109, May 15, 2019.

(56) References Cited

OTHER PUBLICATIONS

Marcy et al., "Nanoliter Reactors Improve Multiple Displacement Amplification of Genomes from Single Cells," PLoS Genetics, 3(9):1702-1708, Sep. 21, 2007.
Martin, "Sepsis, severe sepsis and septic shock: changes in incidence, pathogens and outcomes," Expert Rev. Anti. Infect. Therapy, 10(6):701-706, Jan. 10, 2014.
McGrath et al., "Deterministic lateral displacement for particle separation: a review," Lab Chip, 14(21):4139-4158, Sep. 2014.
MIT.edu [online], "Microfluidics device helps diagnose sepsis in minutes," Jul. 23, 2019, retrieved on Mar. 27, 2023, retrieved from URL<https://news.mit.edu/2019/biosensor-diagnose-sepsis-minutes-0723>, 5 pages.
Motley et al., "Improved Multiple Displacement Amplification (iMDA) and Ultraclean Reagents," BMC Genomics, 15(1):443, Jun. 6, 2014, 10 pages.
Platsidaki et al., "Recent advances in understanding *Propionibacterium* acnes ( *Cutibacterium* acnes) in acne," F1000Research, 7:F1000 Faculty Rev-1953, Dec. 19, 2018, 12 pages.
Puttaswamy et al., "Novel electrical method for early detection of viable bacteria in blood cultures," J. Clin. Microbiology, 49(6):2286-2289, Jun. 2011.
Rackus et al., "Pre-concentration by liquid intake by paper (P-CLIP): a new technique for large volumes and digital microfluidics," Lab Chip, 17(13):2272-2280, Jun. 12, 2017.
Raj et al., "Composite dielectrics and surfactants for low voltage electrowetting devices," Presented at Proceedings of the 2008 17th Biennial University/Government/Industry Micro/Nano Symposium, Louisville, KY, USA, Jul. 13-16, 2008, 4 pages.
Robinson et al., "Integrative genomics viewer," Nat. Biotechnology, 29(1):24-26, Jan. 2011.
Rosselli et al., "Direct 16S rRNA-seq from bacterial communities: a PCR-independent approach to simultaneously assess microbial diversity and functional activity potential of each taxon," Sci. Reports, Aug. 31, 2016, 6:32165.
Shields et al., "Microfluidic cell sorting: a review of the advances in the separation of cells from debulking to rare cell isolation," Lab Chip, 15(5):1230-1249, Mar. 7, 2015.
Simpson et al., "Detecting DNA cytosine methylation using nanopore sequencing," Nat. Methods, 14(4):407-410, Feb. 20, 2017.
Tozaki et al., "Robustness of Digital PCR and Real-Time PCR in Transgene Detection for Gene-Doping Control," Anal. Chemistry, 93(18):7133-7139, Apr. 29, 2021.
Tyler et al., "Evaluation of Oxford Nanopore's MinION Sequencing Device for Microbial Whole Genome Sequencing Applications," Sci. Reports, 8(1):10931, Jul. 19, 2018, 12 pages.
Wick et al., "Completing bacterial genome assemblies with multiplex MinION sequencing," Microbial Genomics, 3(10):e000132, Sep. 14, 2017.
Wilson et al., "Laboratory diagnosis of urinary tract infections in adult patients," Clin. Infect. Diseases, 38(8):1150-1158, Apr. 15, 2004.
Yin et al., "High-Throughput Single-Cell Sequencing with Linear Amplification," Mol. Cell, 76(4):676-690.e10, Sep. 5, 2019.
Yu et al., "Microfluidic Whole Genome Amplification Device for Single Cell Sequencing," Anal. Chemistry, 86(19):9386-9390, Sep. 22, 2014.
Zare et al., "Microfluidic Platforms for Single-Cell Analysis," Ann. Rev. Biomed. Engineering, 12:187-201, Apr. 30, 2010.
Zhang et al., "DEP-on-a-Chip: Dielectrophoresis Applied to Microfluidic Platforms," Micromachines, 10(6):423, Jun. 24, 2019.

* cited by examiner

POINT-OF-CARE DIGITAL MICROFLUIDICS FOR SEPSIS DIAGNOSIS

CROSS-REFERENCE TO RELATED APPLICATIONS

This application is a National Stage application under 35 U.S.C. § 371 of International Application No. PCT/US2021/023123 having an International Filing Date of Mar. 19, 2021, which claims priority from U.S. Provisional Application Ser. No. 62/992,061, filed Mar. 19, 2020. The disclosures of the prior applications are considered part of (and are incorporated by reference in) the disclosure of this application.

BACKGROUND

1. Technical Field

This document relates to digital microfluidics devices for diagnosis of a disease. For example, this document relates to point-of-care digital microfluidics devices for removing target cells from a blood sample and identifying bacterial DNA in the remaining sample to diagnose a disease.

2. Background Information

Sepsis occurs in the body when an immune response, initiated by an infection, causes inflammation to ensue throughout the body. The National Institute of Health (NIH) estimates that at least 1.7 million people in the United States are diagnosed with Sepsis each year, and 25-50% of these patients may die from the condition. According to Centers for Disease Control and Prevention (CDC), one in every three deaths in a hospital are due to Sepsis. The standard approach for identifying Sepsis relies on diagnostic tools, such as vital signs, blood tests, imaging, and lab tests.

The standard approach generally relies on a bacterial culture, which can take days or weeks to complete. In addition, standard methods for detecting and/or identifying a bacterial infection can include steps such as obtaining a culture, conducting quantitative polymerase chain reaction (qPCR), and applying standard sequencing, which often require bulky, costly equipment and are relatively complex and time-consuming. During medical emergencies, it is logistically challenging to have immediate access to standard tests to identify bacterial strains such as those that lead to life-threatening infections in a rapid manner. However, these types of situations are exactly when rapid and accurate disease diagnosis is critical and can prevent secondary deaths caused by undiagnosed, untreated diseases.

SUMMARY

This document provides digital microfluidics (DMF) devices for disease diagnosis, such as Sepsis diagnosis. For example, this document provides point-of-care digital microfluidics devices that can remove white blood cells from a blood sample and identify bacterial DNA in the remaining biological sample to diagnose Sepsis. In various embodiments, the systems, devices, and methods provided herein provide a digital microfluidic platform for a rapid, portable, and automated approach for providing microbial whole genome amplification (WGA) and sequencing (e.g., nanopore sequencing) for Sepsis diagnosis in various settings, such as in an urgent care setting.

The systems, devices, and methods provided herein can provide several advantages for bacterial infectious disease screening. In particular, the DMF devices provided herein can provide a portable point-of-case diagnosis tool to diagnosis a disease, such as Sepsis. In some embodiments, the DMF devices provided herein can allow for a rapid diagnosis of bacterial Sepsis, for example, a diagnosis within hours (e.g., 6 hours) after taking a sample from a patient.

The DMF devices provided herein can be capable of rapidly identifying pathogenic and bacterial infections in human whole blood samples and of identifying genetically driven antibiotic resistance in various embodiments. In some cases, a DMF device described herein can be a single, portable device to perform multiple processes and provide functionalities, normally performed in different laboratories. For example, a DMF device provided herein can be configured to perform several integrated processes, including sample pre-processing, bacterial nucleic acid (e.g., DNA) extraction, nucleic acid (e.g., DNA) amplification, and library construction. In some cases, a device provided herein can be configured to perform multiple processes (e.g., bacterial nucleic acid (e.g., DNA) extraction, nucleic acid (e.g., DNA) amplification, and library construction) as part of a system that employs an automated process.

The systems, devices, and methods described herein can used as a diagnosis tool having a high sensitivity with up to 100 times less than standard? sample size volume at affordable costs that provides critical information for timely medical intervention. In some embodiments, the devices can provide rapid diagnosis using physiological fluids such as blood, saliva, and sputum for detecting bacterial infectious diseases.

In one aspect, a microfluidics device includes a substrate including a first location comprising one or more immobilized analytes, a second location, and a third location. The device also includes an array of electrodes configured to move a biological sample of a mammal from said first location to said second location and from said second location to said third location. The first location is configured to capture at least some cells of said mammal from said sample via said one or more immobilized analytes to form a cell-free sample. The second location is configured to receive said cell-free sample and one or more reagents for performing WGA to form an amplified sample. The third location is configured to receive said amplified sample and one or more reagents for performing library construction to form a sequencing ready sample.

In some embodiments, the device is a digital microfluidic chip. In some embodiments, the biological sample comprise blood. In some embodiments, the biological sample comprises human blood. In some embodiments, the one or more immobilized analytes comprise an anti-CD45 antibody. In some embodiments, the at least some cells comprise white blood cells, red blood cells, platelets, or combinations thereof. In some embodiments, the at least some cells comprise white blood cells.

In some embodiments, the one or more analytes are configured to bind from about 1,000 to about 100,000 cells per each droplet of the biological sample. In some embodiments, the one or more immobilized analytes are configured to bind from about 5,000 to about 50,000 cells per each droplet of the biological sample. In some embodiments, the one or more immobilized analytes are configured to bind from about 7,000 to about 25,000 cells per each droplet of the biological sample. In some embodiments, the one or more immobilized analytes are configured to bind from about 10,000 to about 15,000 cells per each droplet of the biological sample.

In some embodiments, the array of electrodes comprise chrome. In some embodiments, the array of electrodes comprise a coating disposed on the array of electrodes. In some embodiments, the coating comprises an insulative material. In some embodiments, the coating comprises a hydrophobic material. In some embodiments, the coating comprises indium tin oxide.

In some embodiments, the array of electrodes are configured to define one or more microfluidic channels on the substrate. In some embodiments, the device is further configured to transfer the sequence ready sample. In some embodiments, the second and third locations are at different locations on the substrate. In some embodiments, the second and third locations are the same location.

In another aspect, a method of preparing a biological sample for diagnosis of a disease includes: providing a biological sample on the substrate of the device of claim 1; and moving said biological sample from the first location to the second location, and from the second location to the third location. In some embodiments, the second location and the third location are the same location. In some embodiments, the method further includes moving one or more reagents from an initial location to the second location, the third location, or both. In some embodiments, the method further includes moving one or more reagents to the second location for performing WGA. In some embodiments, the method further includes moving one or more reagents to the third location for performing library construction. In some embodiments, the moving the biological sample from one location to another location comprises activating and deactivating electrodes in a path defined between the first and second locations.

In some embodiments, the method further includes moving the biological sample from the second location to the third location. In some embodiments, further includes capturing said at least some cells of said mammal from said sample via said one or more immobilized analytes to form a cell-free sample at the first location. In some embodiments, further includes performing WGA at the second location to form the amplified sample. In some embodiments, further includes performing library construction to form the sequencing ready sample.

In some embodiments, the biological sample comprises blood. In some embodiments, the biological sample comprises serum. In some embodiments, the biological sample comprises saliva. In some embodiments, the providing comprises placing one or more droplets of the biological sample on the substrate. In some embodiments, the method further includes obtaining the blood sample from the patient. In some embodiments, the patient is a mammal. In some embodiments, the patient is a human.

In some embodiments, the cell-free biological sample comprise less than 10,000 cells per droplet. In some embodiments, the cell-free biological sample comprise less than 7,000 cells per droplet. In some embodiments, the cell-free biological sample comprise less than 5,000 cells per droplet. In some embodiments, the cell-free biological sample comprise less than $5\times10^9$ cells per liter (cells/L). In some embodiments, the cell-free biological sample comprise less than $3\times10^9$ cells/L. In some embodiments, the cell-free biological sample comprise less than $1\times10^9$ cells/L. In some embodiments, the cell-free biological sample comprise less than $1\times10^6$ cells/L. In some embodiments, the cell-free biological sample comprise less than $1\times10^3$ cells/L.

In some aspects, a procedure comprising performing any of the methods provided herein during an emergency medicinal procedure, therapeutic response monitoring, disease prognosis, or early detection of a cancer.

Other advantages of the devices provided herein include its suitable use in a wide range of applications, including emergency medicine, therapeutic response monitoring in intensive care unit and critical disease diagnosis and prognosis.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 3A illustrates the electrode arrays, and FIG. 3B indicates the reservoirs for the sample, waste, mix, rapid adapter, lysis buffer, stop solution, DNA polymerase, and WBC collection.

FIG. 7A is a photo showing a close-up of a DMF device inserted into the Dropbot system, with fluids on reservoir electrodes. FIG. 7B is a cross-sectional diagram of a DMF device, showing fluid manipulation between the top and bottom substrates.

FIG. 8A is a graph plotting the amount of DNA obtained after amplification in-tube and on-chip. FIG. 8B is a graph plotting the amount of sequencing data generated for samples amplified in-tube for 2 hours. FIG. 8C is a graph plotting the percent of sequencing reads that passed quality control (Qscore>7) for samples amplified in-tube and on-chip. FIG. 8D is a graph plotting the amount of sequencing data generated for samples amplified on-chip for 2 hours or 30 minutes.

FIG. 9A is a graph plotting the contamination profile for samples with different starting amounts of *C. glutamicum* DNA amplified on-chip and in-tube. The results show the profile after 30 minutes of sequencing. Sequencing failed for samples with <1 pg starting DNA amplified in-tube. FIG. 9B is a graph plotting the contamination profile of 100 pg *C. glutamicum* DNA amplified for 2 hours on-chip. Extended sequencing times led to increased numbers of target species reads, with marginal increases of contaminant reads.

DETAILED DESCRIPTION

This document provides point-of-care digital microfluidics (DMF) devices that can be used to quickly diagnose a disease, such as Sepsis. The point-of-care DMF devices (as well as systems) provided herein can be used to diagnose a disease within a short period of time (e.g., in about 6 hours or less), as well as to provide a portable means for diagnosis.

In various embodiments, the DMF systems and devices provided herein can provide a reliable diagnosis of Sepsis from a biological sample by producing a cell-free specimen and performing subsequent bioinformatic analysis on the cell-free specimen. A "cell-free" specimen as used herein refers to a biological product produced after a desired number or amount (e.g., at least 50%, at least 75%, at least 80%, at least 85%, at least 90%, at least 95%, at least 96%, at least 97%, at least 98%, or at least 99%) of target cells (e.g., cells that contain DNA, such as white blood cells) has been removed from a biological sample, such that the "cell-free" specimen has a reduced number of the target cells that would otherwise be present in the biological sample. Reducing the number of one or more particular types of cells from a biological sample prior to performing genomic processing (e.g., genome amplification and/or nanopore sequencing) can advantageously reduce noise and reduce test time during the diagnosis of a disease, such as Sepsis. In some cases, the devices and methods provided herein can identify the source of a bacterial infection in human blood samples within a few hours.

Figure 1:
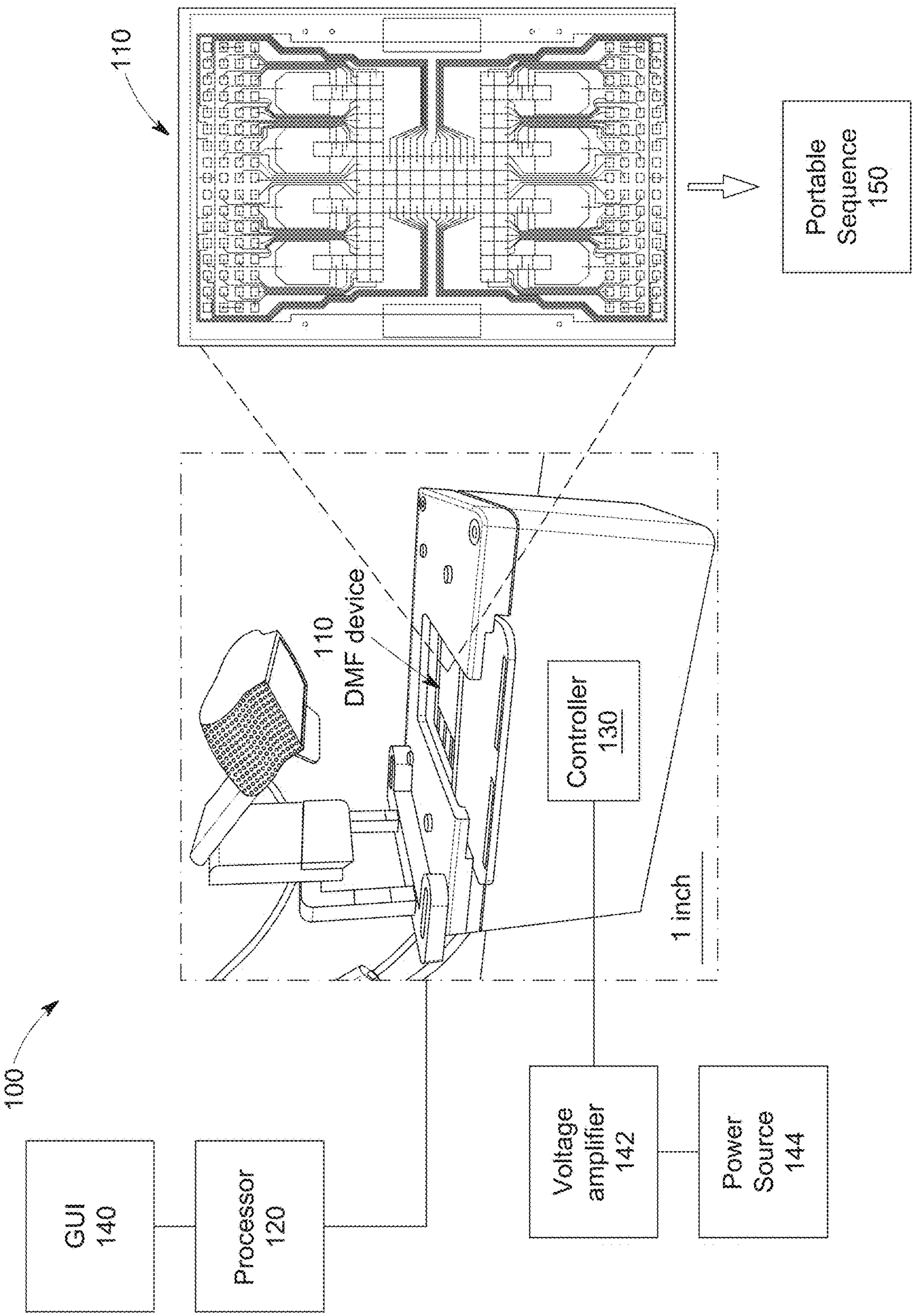
FIG. 1 shows a photo of an example digital microfluidics (DMF) device, according to some embodiments.

FIG. 1 shows an example of a portable system 100 comprising a DMF device 110 (e.g., a microfluidic chip) configured for diagnosing a disease (e.g., Sepsis). System 100 is configured for programmable control droplet manipulation through use of a microfluidics controller and graphic user interface. In various embodiments, system 100 can be a portable system that is easily transported from one location to another. In some embodiments, system 100 can be used to identify any bacterial infectious disease that may be identified through bioinformatics analysis of blood, saliva, or other physiological fluids (e.g., urine, plasma, serum, or cerebrospinal fluid).

System 100 includes a processor 120 for compiling information and processing data. System 100 also includes a control system 130 for executing programs to perform activation/deactivation of electrodes of DMF device 110 that manipulate microfluidic flow (e.g., create microfluidic channels). A graphic user interface (GUI) 140 is also provided for visually displaying microfluidic information to a user and receiving input from the user. System 100 includes a voltage amplifier 142 and a power source 144 to provide and amplify power delivered to the system, applying an electrostatic driving force for influencing microfluidics flow in DMF device 110. System 100 can optionally include a portable sequencer 150 for, without limitation, bacterial identification and analysis of their genetically encoded antibiotic resistance genes. Components of system 100 may be readily assembled together, disassembled, and/or reassembled. System 110 is configured for rapid diagnosis of a disease (e.g., bacterial Sepsis) within a short period of time, for example, about 6 hours or less (e.g., about 5 hours or less, about 4 hours or less, about 3 hours or less, about 2 hours or less, about 1 hour or less, about 30 minutes or less, about 15 minutes or less, or about 10 minutes or less).

As shown in FIG. 1, DMF device 110 is a microfluidic chip (which also can be referred to as a platform). DMF device 110 includes a substrate having a planar surface that includes a plurality of discrete areas. The discrete areas are formed by an array of electrodes coated with a hydrophobic insulator. Each discrete area is formed by at least one electrode that can be readily activated, deactivated, and/or reactivated. Activation of the electrodes creates an electric current at the corresponding discrete region(s), which results in droplet movement, as desired, along the substrate. By using electric current to drive droplet movement, a DMF device can be configured to, based on electrowetting principles, rapidly move, mix, and separate liquid droplets that facilitates reliable, controllable liquid transport. In some embodiments, a DMF device provided herein can generate a plurality of fluidic channels on its substrate based on specific pathways formed by a given sequence of electrode activations and deactivations.

DMF device 110 can be configured to receive a liquid sample, such as a biological sample, a reagent, or a buffer. The liquid sample can be a biological sample, such as blood, saliva, plasma, serum, or the like. The liquid samples can be provided in the form of one or multiple droplets. In some embodiments, the substrate of DMF device 110 can receive the sample in one or more designated areas, such as a reservoir. The designated area may be labeled on the substrate, in some embodiments.

DMF device 110 can include one or more reservoirs, wherein each reservoir is configured to receive and hold an amount of liquid, such as a reagent, in excess of one droplet (e.g., an amount equivalent to 3 droplets, 4 droplets, 5 droplets, 10 droplets, 15 droplets, 20 droplets, 25 droplets, 30 droplets, 40 droplets, or 50 droplets or more). In some cases, the reservoirs can be configured to hold one or more liquids used for WGA and/or sequencing (e.g., nanopore sequencing), which will be discussed in later sections.

Figure 2A:
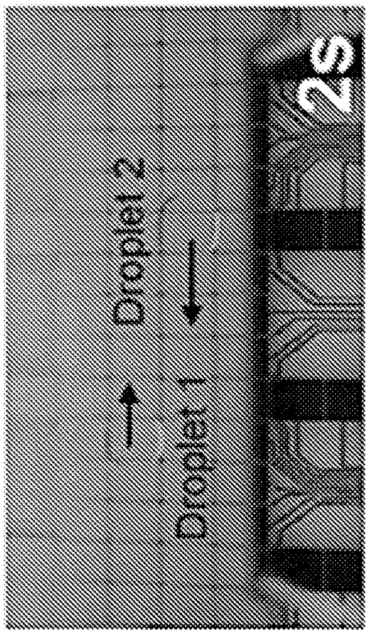
FIGS. 2A-2F includes a series of photos showing time-lapse images of droplet transport, merging, and splitting in the DMF device of FIG. 1 at 2 seconds (FIG. 2A), 4 seconds (FIG. 2B 6 seconds (FIG. 2C), 8 seconds (FIG. 2D), 10 seconds (FIG. 2E), and 12 seconds (FIG. 2F), according to some embodiments.
Figure 2B:
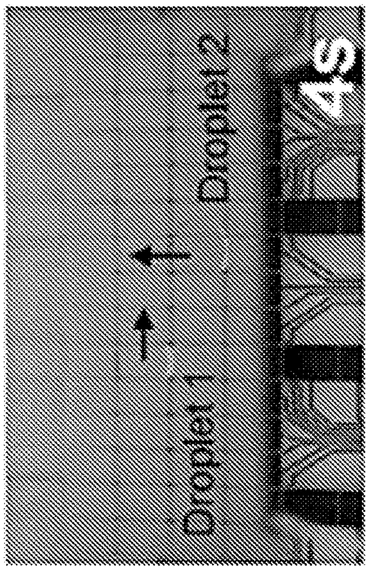
Figure 2C:
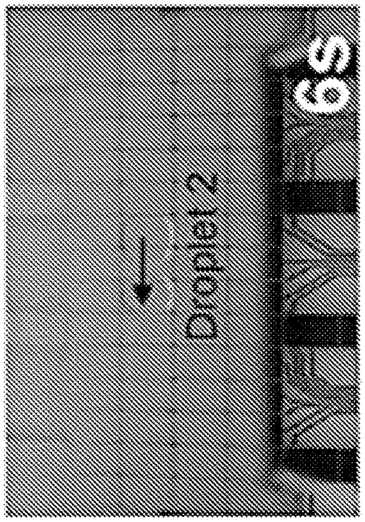
Figure 2D:
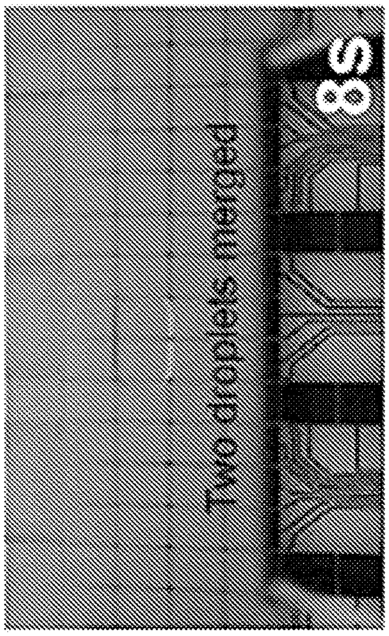
Figure 2E:
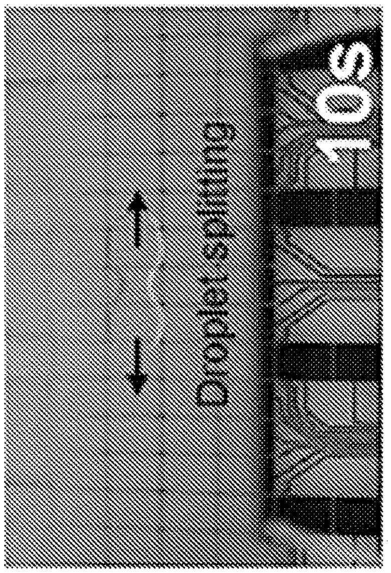
Figure 2F:
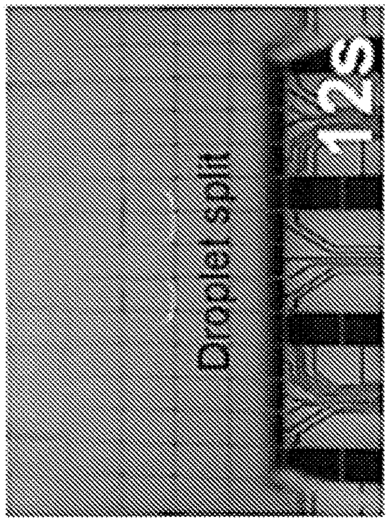

In some embodiments, a DMF device provided herein can include an array of electrodes coupled to the substrate, where the electrodes are configured for agitating, mixing, moving, and/or splitting a liquid sample on a substrate. For example, as shown in FIGS. 2A-2F, time-elapsed images of droplets show transport, merging and splitting on the substrate of a DMF device. Two droplets along the substrate can be moved (FIGS. 2A-C) or merged (FIG. 2D). Alternatively, a single droplet can be split to form multiple droplets (FIGS. 2E-F). Droplet movement is driven by a series of electrode activation on or adjacent to the substrate that can be programmed through a graphic user interface. For example, rapid activation and deactivation of the same electrode can promote agitation of the liquid sample, while sequential activation and deactivation of adjacent electrodes can promote droplet movement in a desired direction along the substrate. The substrate can include visible markings (e.g., grid-like markings) to identify to the user the relative size and/or general location of the electrodes that make up the array.

Figure 3B:
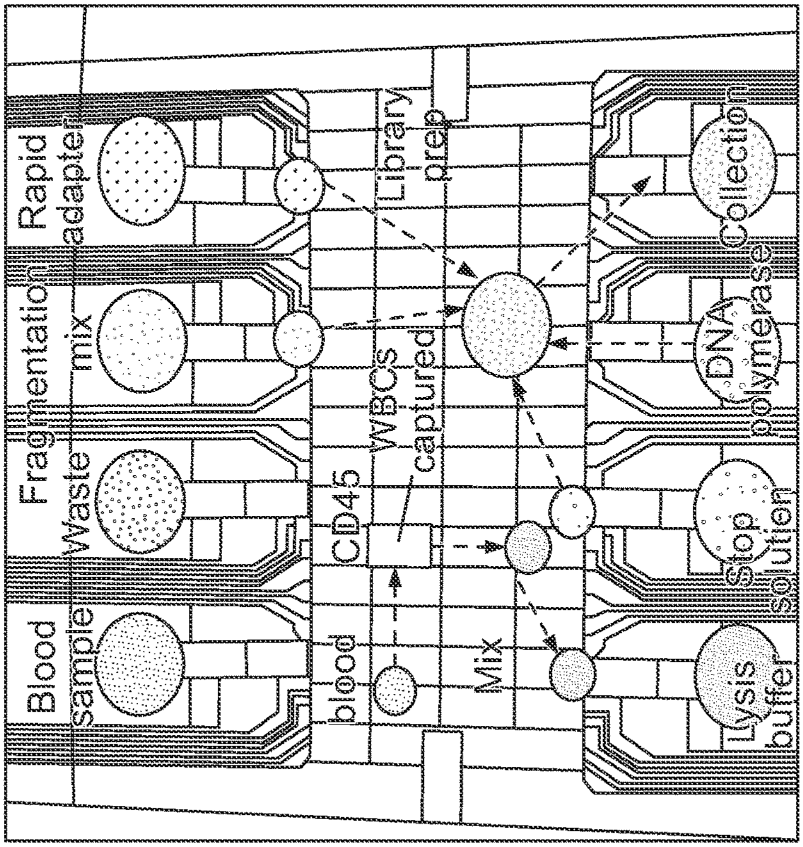
FIGS. 3A-3B are photos showing examples of a DMF device, depicting a sample (e.g., a blood sample) moving across a substrate (shown by arrows) that includes an immobilized CD45 antibody region for capturing white blood cells (WBCs), according to some embodiments.
Figure 3A:
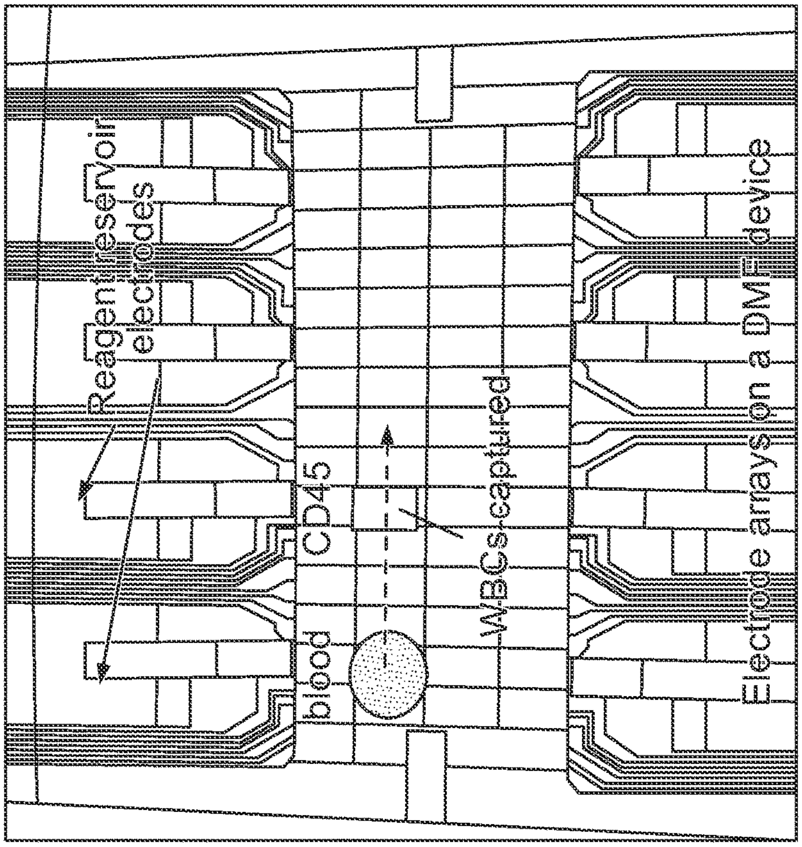

DMF device 110 further includes one or more analytes immobilized on the substrate. Such an analyte can be selected based on its ability to bind to particular target cells to be removed from a sample. As shown in FIGS. 3A-3B, a blood droplet on a substrate of an exemplary DMF device can be moved across a portion of the substrate where analytes are immobilized. One or more analytes may be selected to bind with mammalian cells, for example, human cells. The analytes can be selected to bind with blood cells. In some embodiments, the analytes can be selected to bind with white blood cells, such as human white blood cells. In various embodiments, the analytes can be selected to bind with mammalian cells that have particular CD markers. A non-limiting example of a suitable analyte is an anti-CD45 antibody. Example of methods for using anti-CD45 antibodies for white blood cell capture in microfluidic devices are described elsewhere (see e.g., Gawk et al., "Progress in Circulating Tumor Cell Research Using Microfluidic Devices,"*Micromachines* (*Basel*) 9(7):353 (July 2018); Lee et al., "An integrated microfluidic chip for one-step isolation of circulating tumor cells," *Sensors and Actuators B: Chemical*, vol. 238 (January 2017); and US Pat. Publication No. 2015/0260711, titled "Microfluidic Device For Cell Separation And Uses Thereof"), which are incorporated by reference in their entirety. In some embodiments, the analytes are configured to bind to about 1,000 to about 100,000 cells per droplet (e.g., about 5,000 to about 50,000 cells per droplet, about 7,000 to about 25,000 cells per droplet, or about 10,000 to about 15,000 cells per droplet). Inclusion of one or more target-cell-binding analytes can advantageously provide the DMF devices with improved detection of specific disease-causing bacteria, such as those associated with Sepsis, by removing select target cells from the sample before bioinformatic analysis is performed.

Figure 4:
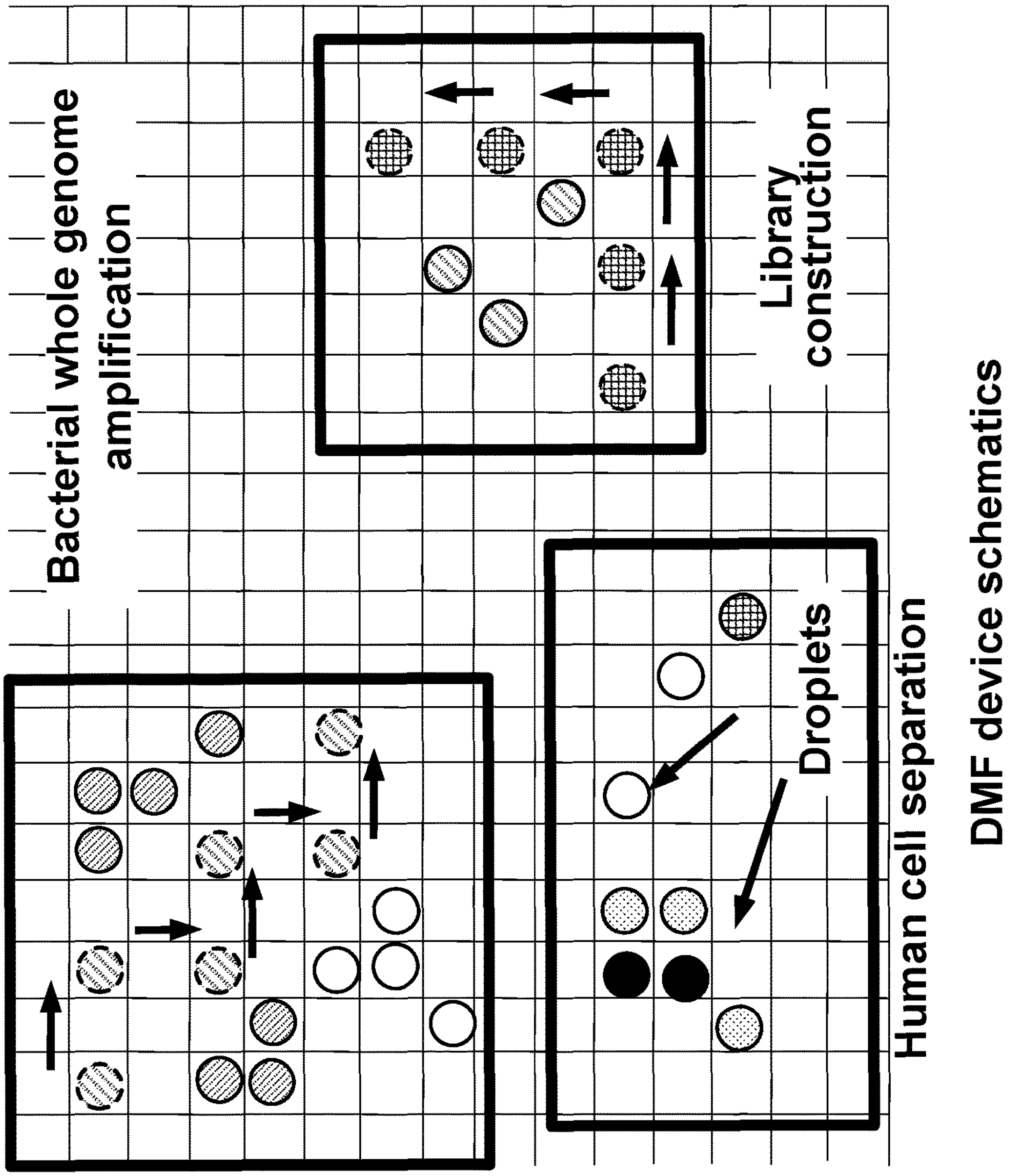
FIG. 4 depicts an example schematic platform showing several processes, including cell separation, bacterial WGA, and library construction, which can be performed by a DMF device provided herein according to some embodiments.

FIG. 4 shows a schematic platform of an exemplary DMF device. The schematic platform illustrates one or more functionalities provided by the substrate of the DMF device that facilitates a diagnosis of a disease. Three functionalities of the platform include cell separation, sample processing, and library construction (see also FIG. 3B). Each functionality can be designated to occur at a specific region of the substrate, such as at a cell separation region, a processing region, and a library construction region. The cell separation region can include one or more areas of the substrate configured for removing specific human cells (e.g., white blood cells) from a biological sample (e.g., blood). The processing region can include one or more areas of the substrate configured for processing the biological sample. In some embodiments, the processing region can be designed to perform one or more sample processing steps that include, but are not limited to, bacterial nucleic acid (e.g., DNA) extraction, genome or nucleic acid amplification (e.g., WGA), and/or sequencing (e.g., nanopore sequencing) of the nucleic acid from the biological sample.

Incorporation of WGA functionality within a microfluidic device can be performed as described elsewhere (see e.g., Gorgannezhad et al., "Microfluidic-Based Nucleic Acid Amplification Systems in Microbiology,"*Micromachines* 10(7), 408 (July 2019); Yu et al., "Microfluidic Whole Genome Amplification Device for Single Cell Sequencing," *Analytical Chemistry,* 86, 19 (September 2014); and WIPO Publication No. WO 2017/205304A1, titled "Single cell whole genome amplification via micropillar arrays under flow conditions", which are incorporated by reference in their entirety).

The library construction region can include one or more areas of the substrate configured for compiling data collected from the processing region. Any appropriate method can be applied to incorporate and use a DNA library preparation functionality within a microfluidic device, including those methods described elsewhere (see e.g., Kim et al., "A Microfluidic DNA Library Preparation Platform for Next-Generation Sequencing," *PloS One* (July, 2013); and US Application Publication No. US 2013/0225452, titled "Method of Preparing a Nucleic Acid Library", which are incorporated by reference in their entirety). In various embodiments, the devices provided herein can be configured for providing library transfer to a portable sequencer, for example, as described elsewhere (e.g., U.S. Patent Application Publication No. 2013/0225452). Commercial portable sequencers are available, such as MinION, which is manufactured by Oxford Nanopore Technologies. In some embodiments, a DMF device provided herein can include multiple cell separation, processing, and library construction regions. In some embodiments, a DMF device provided herein can be configured to perform cell separation, processing, and library construction without the use of any designated regions on the substrate. In some embodiments, each processing region can be located within a distinct area of the substrate that is exclusive to other regions.

In some embodiments, the device provided herein includes a substrate that includes a first location with one or more immobilized analytes, a second location, and a third location, and an array of electrodes configured to move a biological sample of a mammal from the first location to the second location and from the second location to the third location, The first location can be configured to capture at least some cells from the sample via the one or more immobilized analytes to form a cell-free sample. In some embodiments, the cell-free biological sample includes about 100 cells per droplet to about 10,000 cells per droplet (e.g., about or less than 7,000 cells per droplet, about or less than 5,000 cells per droplet, about or less than 3,000 cells per droplet, about or less than 1,000 cells per droplet, about or less than 500 cells per droplet, about 100 to about 1000 cells per droplet, about 1000 to about 3000 cells per droplet, about 3000 to about 5000 cells per droplet, or about 5000 to about 10,000 cells per droplet). In some embodiments, the cell-free biological sample contains less than $5\times10^9$ cells per liter (cells/L). In some embodiments, the cell-free biological sample contains from about $1\times10^3$ cells/L to about $3\times10^9$ cells/L (e.g., less than $1\times10^9$ cells/L, less than $1\times10^6$ cells/L, about or less than $1\times10^3$ cells/L, about $1\times10^3$ to about $1\times10^4$ cells/L, about $1\times10^4$ to about $1\times10^5$ cells/L, about $1\times10^5$ to about $1\times10^6$ cells/L, about $1\times10^6$ to about $1\times10^7$ cells/L, about $1\times10^7$ to about $1\times10^8$ cells/L, or about $1\times10^8$ to about $1\times10^9$ cells/L).

The second location can be configured to receive a cell-free sample and one or more reagents for performing WGA to generate an amplified sample. The third location can be configured to receive the amplified sample and one or more reagents for performing library construction to form a sequencing ready sample.

In some cases, the DMF devices provided herein can be used for diagnosing a disease (e.g., Sepsis) by performing the following steps. A biological sample (e.g., blood) is placed on a substrate of the DMF device. The sample may be placed in a designated receiving region of the substrate, such as a reservoir electrode. The biological sample can be in the form of one or more droplets.

The received sample is then pretreated by moving the sample droplet across a pretreatment region having one or more immobilized analytes (e.g., anti-CD45 antibodies) configured to bind to target cells within the biological sample. The sample may be agitated in the pretreatment region to promote cell binding, which can promote target cell removal from the sample. Cell binding agitation can occur for about 1 second to about 10 minutes (e.g., from about 5 seconds to about 60 seconds, from about 1 minute to about 5 minutes, or from about 5 minutes to about 10 minutes). After cell-binding has taken place, a cell-free sample can be further processed for bioinformatic analysis.

To facilitate bioinformatics analysis, the sample can be combined with at least one liquid agent in one or more mixing steps to facilitate WGA or library construction. Exemplary liquid agents can include a lysis buffer, a stop solution, a polymerase solution (e.g., a solution containing a DNA polymerase), a fragmentation mixture, a rapid adapter mixture, or any combination thereof.

Potential bacteria within the sample can be lysed using any suitable method. For example, a lysis buffer may be mixed with the sample for lysing. In some embodiments, suitable lysis buffers include one or more active agents including, without limitation, enzymes, alkalines (e.g., NaOH or other solutions with a pH>7), dithiothreitol or the like, and any combination thereof. Commercial lysis buffers are also available in Repli-G single cell kits, which are manufactured by Qiagen N.V. In some embodiments, the lysis buffer can include from about 10 μ/L to about 500 U/μL (e.g., about 20 U/μL to about 400 U/μL, about 50 U/μL to about 300 U/μL, about 100 U/μL to about 300 U/μL) active agent. In some embodiments, the lysis buffer can include from about 10 mM to about 500 mM (e.g., about 20 mM to about 400 mM, about 50 mM to about 300 mM, about 100 mM to about 300 mM) active agent.

In some embodiments, after a lysis buffer has been introduced to the sample, the sample can be mixed with a stop solution to stop enzymatic activity by, for example, denaturing the enzyme used for lysis. Non-limiting examples of a stop solution can include solutions containing sodium dodecyl sulfate (e.g., 3% (w/v) sodium dodecyl sulfate), or commercially available stop solutions (e.g., stop solution in kits provided by ThermoFisher Scientific Co. or stop solutions available in Repli-G single cell kits, which are manufactured by Qiagen N.V.). Suitable stop solutions include, but are not limited to, solutions containing acids, such as HCl, to neutralize the lysis buffer. The sample can be agitated with the stop solution for any suitable time, for example, about 1 minute to about 10 minutes or more (e.g., about 2 minutes, 3 minutes, 4 minutes, 5 minutes, 6 minutes, 7 minutes, 9 minutes, about 10 minutes or more, about 1 to about 3 minutes, about 3 to about 5 minutes, about 5 to about 7 minutes, or about 7 to about 10 minutes).

The lysed, cell-free sample can also be mixed with a solution containing at least one DNA polymerase for enzymatic synthesis of DNA from deoxyribonucleotides for WGA. Commercial DNA polymerases for enzymatic synthesis of DNA from deoxyribonucleotides for WGA can be found, for example, in Repli-G single cell kits, which are manufactured by Qiagen N.V. In some embodiments, the sample can be mixed with a solution containing at least one DNA polymerase for PCR-based WGA. In some embodiments, the sample can be mixed with a solution containing at least one DNA polymerase solution for multiple displacement amplification WGA. The sample can be agitated with at least one DNA polymerase solution for any suitable time, for example, about 1 hour to about 5 hours (e.g., about 2 hours, 3 hours, 4 hours, about 5 hours or more, about 1 to about 2 hours, about 2 to about 3 hours, about 3 to about 4 hours, or about 4 to about 5 hours).

The lysed, cell-free sample can also be mixed with a fragmentation mixture and subjected to a thermocycling process. Suitable fragmentation solutions include any agent that can break long strands of DNA into shorter pieces. Fragmentation solutions are available in Qiagen Repli-G single cell kits, for example. In some embodiments, the fragmentation solution contains one or more enzymes suitable for fragmenting DNA strands. The sample can be agitated with a fragmentation mixture for about 5 seconds to about 10 minutes or more (e.g., about 10 seconds, 20 seconds, 30 seconds, 40 seconds, 50 seconds, 1 minute, about 2 minutes, 3 minutes, 4 minutes, 5 minutes, 6 minutes, 7 minutes, 9 minutes, about 10 minutes or more, about 10 to about 30 seconds, about 30 seconds to about 1 minute, about 1 to about 3 minutes, about 3 to about 5 minutes, about 5 to about 7 minutes, or about 7 to about 10 minutes). The thermocycling process can include a first heating step at a first temperature (e.g., about 20-40° C.), followed by a second heating step at a second temperature (e.g., about 70-90° C.), followed by a rapid cooling step (e.g., cool sample with ice). Each thermocycling step can last about 30 seconds to about 5 minutes or more (e.g., about 1 minute, 2 minutes, 3 minutes, 4 minutes, 5 minutes or more, about 30 seconds to about 1 minute, about 1 to about 2 minutes, about 2 to about 3 minutes, about 3 to about 4 minutes, or about 4 to about 5 minutes).

The lysed, cell-free sample can be further mixed with a rapid adapter mixture. Commercial rapid adapter mixtures can be found in Repli-G single cell kits, which are manufactured by Qiagen N.V. The sample can be agitated with a rapid adapter mixture for about 5 seconds to about 10 minutes or more (e.g., about 10 seconds, 20 seconds, 30 seconds, 40 seconds, 50 seconds, 1 minute, about 2 minutes, 3 minutes, 4 minutes, 5 minutes, 6 minutes, 7 minutes, 9 minutes, 10 minutes or more, about 10 to about 30 seconds, about 30 seconds to about 1 minute, about 1 to about 3 minutes, about 3 to about 5 minutes, about 5 to about 7 minutes, or about 7 to about 10 minutes). The thermocycling process can include a first heating step at a first temperature (e.g., about 20-40° C.), followed by a second heating step at a second temperature (e.g., about 70-90° C.), and followed by a rapid cooling step (e.g., cool sample with ice). Each thermocycling step can last about 30 seconds to about 5 minutes or more (e.g., 1 minute, 2 minutes, 3 minutes, 4 minutes, 5 minutes or more, about 30 seconds to about 1 minute, about 1 to about 3 minutes, or about 3 to about 5 minutes).

The ratio of the amount of sample combined with any of the liquid agents discussed herein can range from 1:10 to about 10:1 (e.g., about 1:9, 1:8. 1:7, 1:6, 1:5, 1:4, 1:3, 1:2, 1:1, 2:1, 3:1, 4:1, 5:1, 6:1, 7:1, 8:1, or 9:1). For example, in some embodiments, a 1 μL droplet of blood may be mixed with 1 μL droplet of a lysis buffer, 1 μL droplet of a stop solution, 6 μL of DNA polymerase, 1 μL droplet of fragmentation mix, and 1 μL droplet of rapid adapter, respectively, in a DMF device. Any appropriate method can be applied to perform WGA using the systems and devices provided herein, including methods described elsewhere (see e.g., Gorgannezhad et al., supra; Yu et al., supra; and WIPO Publication No. WO 2017/205304 A1, which are incorporated by reference in their entirety).

Any appropriate method can be applied to incorporate and use a DNA library preparation functionality within the systems and devices provided herein, including techniques described elsewhere (see e.g., Kim et al., supra); and US Application Publication No. US 2013/0225452).

EXAMPLES

Example 1. Bacterial Reads on Blood Sample

Direct nanopore sequencing was conducted on a human blood sample to obtain baseline results on detectable bacterial reads (see Table 1 below). A clinical blood sample from a patient with myocardial infection was directly sequenced, and only 0.0347% of the total 302,604 reads were detected as bacteria, while the vast majority of reads appeared to be from human components. Direct nanopore sequencing was performed on 1 mL of blood sample spiked with 1,000 and 10,000 *E. coli* cells, respectively, but resulted in a very low number of bacterial reads.

TABLE 1

| Sample | Total raw reads | Human reads | Bacterial reads | Total human reads | Total bacterial reads |
|---|---|---|---|---|---|
| Blood (myocardial infarction) | 302604 | 99.80% | 0.03% | 301998 | 105 |
| Blood spiked with 1,000 *E. coli* | 9006 | 96.40% | 0.04% | 8682 | 3 |
| Blood spiked with 10,000 *E. coli* | 4957 | 98.90% | 0.26% | 4902 | 12 |

The results of the sequencing data were not suitable for downstream bioinformatic analyses, and thus would not lead to the detection of bacteria. It was reported that when a patient begins to show clinical symptoms of Sepsis, the concentration of bacteria in blood is very low (only 1 to 100 CFU/mL in adults and <10 CFU/mL in neonates). Therefore, the infectious agents would remain undetected using direct sequencing.

Example 2. Bacterial Reads on a Blood Sample Using a DMF Device

The following procedure was used to prepare a blood sample for determining the bacterial reads associated with using a DMF device.

1. A 1 μL droplet of human blood was placed on the reservoir electrode using a pipette.
2. The blood droplet was moved to the electrode with anti-CD45 antibodies, and the droplet was agitated by turning on and off the electrode.
3. A 1 μL droplet of lysis buffer containing lysozyme, alkaline (e.g., NaOH or another solution with a pH>7), and dithiothreitol was mixed with the blood droplet by agitating through turning on and off the electrodes for 3 minutes.
4. A 1 μL droplet of stop solution containing HCL was mixed into the sample by turning on and off the electrodes for 3 minutes.
5. DNA polymerase (6 μL; Qiagen Repli-G single cell kit) was mixed with the sample by agitating for 2 hours.
6. A 1 μL droplet of fragmentation mix (Qiagen Repli-G single cell kit) was mixed into the sample by agitation using the electrodes for 1 minute. The device was placed on a heating plate at 30° C. for 1 minute, followed by 80° C. for 1 minute. The device was then placed on ice for 1 minute.
7. A 1 μL droplet of rapid adapter mixture was added into the sample and mixed electrode agitation for 5 minutes.
8. The sample was moved to the collection electrode, and a pipette was used to transfer the sample for loading into a MinION Nanopore sequencer (Oxford Nanopore Technologies).

Following the steps described above, WGA was performed on 0.5 ng lambda DNA (equivalent to the genomic material in ~10,000 *E. coli* cells) in a DMF device.

The results showed that the number of reads of the target strains drastically increased and were within an acceptable range (e.g., a minimum range value of at least 2,000-3,000 reads) for performing bioinformatic analyses, as shown in Table 2.

TABLE 2

| name | numReads |
|---|---|
| *Escherichia coli* | 109378 |
| synthetic construct | 34121 |
| *Escherichia coli* 'BL21-Gold(DE3)pLysS AG' | 5006 |
| *Escherichia* | 4138 |
| *Enterobacteriaceae* | 1927 |
| *Escherichia albertii* | 972 |
| *Escherichia coli* B | 772 |

Example 3—Amplification and Sequencing of 10 Femtograms of Bacterial DNA within 3 Hours Using a DMF Platform

Materials and Methods

Cell Culture and DNA Extraction

*Corynebacterium glutamicum* ATCC 13032 was cultured in LB broth (Research Product International) at 37° C. in a shaker incubator (Thermo Fisher). *Porphyromonas somerae* ATCC BAA1230 was cultured in chopped meat carbohydrate broth (DB) at 37° C. in an anaerobic chamber (Coy). Both cultures were harvested during log phase (~$10^7$/mL) and pelleted at 10,000 g for 3 minutes at 4° C., followed by supernatant removal. DNA was extracted using DNeasy Powersoil Kit (Qiagen) following the manufacturer's instructions. Extracted *C. glutamicum* and *P. somerae* DNA was diluted to 100 pg/μL, 10 pg/μL, 1 pg/μL, 100 fg/μL and 10 fg/μL in nuclease-free water (Ambion). *Escherichia coli* bacteriophage lambda DNA was included in the Oxford Nanopore Technologies Rapid Sequencing Kit (ONT, SQK-RAD004). DNA mixture samples were produced by diluting and mixing the extracted DNA from these three species.

DMF Device Microfabrication

The DMF device layout was designed in AutoCAD (Autodesk), and the electrode contact pads were placed to fit into a DropBot system (Fobel et al., *Applied Physics Letters* 102(19): 193513, 2013). The DMF device was microfabricated on a 2"×3" glass slide pre-coated with a 200 nm chromium layer, with an AZ1500 photoresist layer (Telic Company) as a bottom plate, and an indium-tin oxide (ITO)—coated glass slide (Delta Technologies) used as a top plate. The electrodes were photolithographically patterned on the bottom plate in a mask aligner (KLOE), developed in 1:4 MF 351 developer (Microposit) and etched in CR-Chrome Etch (KMG Electronic Chemicals). Each interdigitated electrode was 2.2 mm×2.2 mm in size. The bottom plate was coated with 5 μm Parylene C (Specialty Coating Systems). 1 mm through-holes were drilled (MicroLux) on the top plate as inlets and outlets of the device. The patterned side of the bottom plate and the ITO side of the top plate were spin coated (1000 rpm, 60 seconds) with 2.25% type M fluoropolymer CYTOP solution (Bellex International Corporation) and incubated on a hotplate at 180° C. for 15 minutes. A copper tape (76.2 μm thick) and an electrically conductive adhesive transfer tape (3M, 102 μm thick) were used as spacers between the top and bottom plates. All sides of the device were sealed using epoxy glue and incubated for an hour at room temperature.

DMF Experimental Setup

Figure 5:
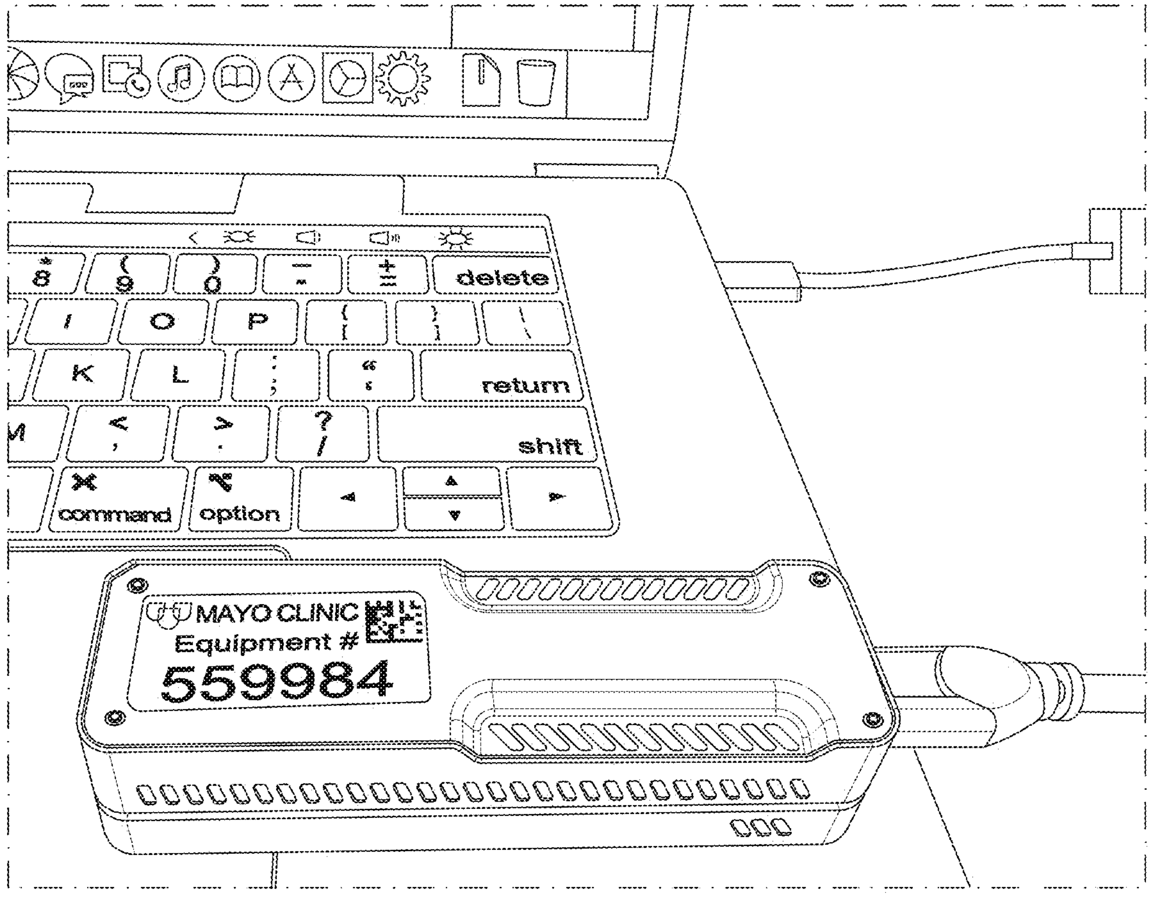
FIG. 5 shows a photo of a portable sequencer connected to a laptop, according to some embodiments.
Figure 6:
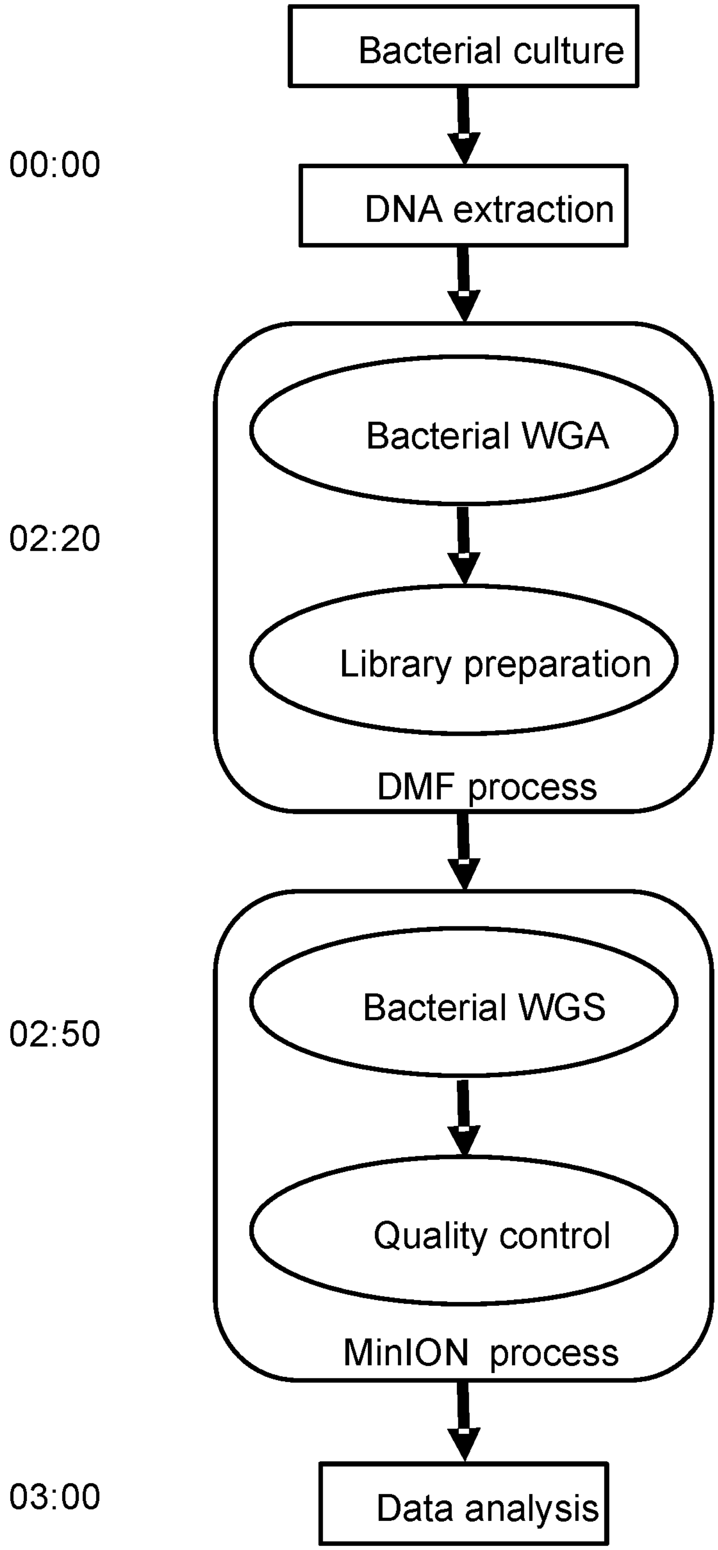
FIG. 6 is a flow diagram depicting the workflow in a method for bacterial whole genome amplification (WGA) in a DMF device, with whole genome sequencing (WGS) in MinION sequencer. The process is completed within 3 hours.

The overall workflow of using the DMF platform for rapid low-abundance bacterial WGA and MinION sequencing is illustrated in FIG. 6. Briefly, the DMF device was operated by a Dropbot system (Sci-bot Inc.; Fobel et al., supra) that consisted of electrical circuitry compacted into a portable black case (5.7"×4"×3"). The Dropbot system was connected to a laptop through USB cable (see, e.g., FIG. 5) to control the DMF device via MicroDrop software. A 2"×3" DMF device was inserted into the Dropbot system, where the user can set parameters (e.g., voltage, frequency, timing) to operate the DMF device to perform droplet transport, splitting and mixing in a programmed manner based on electrowetting principles (Cho et al., J *Microelectromech Syst* 12 (1):70-80, 2003).

Figure 7A:
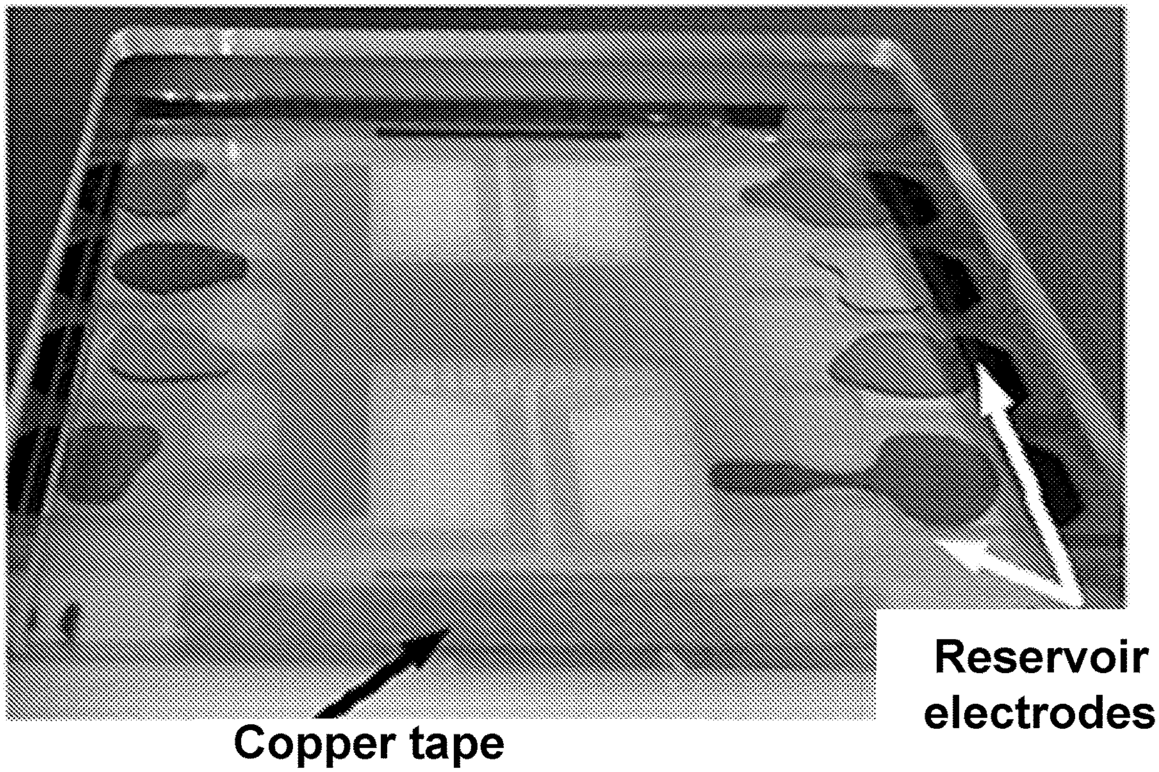
FIGS. 7A and 7B show an overview an embodiment of a DMF device.
Figure 7B:
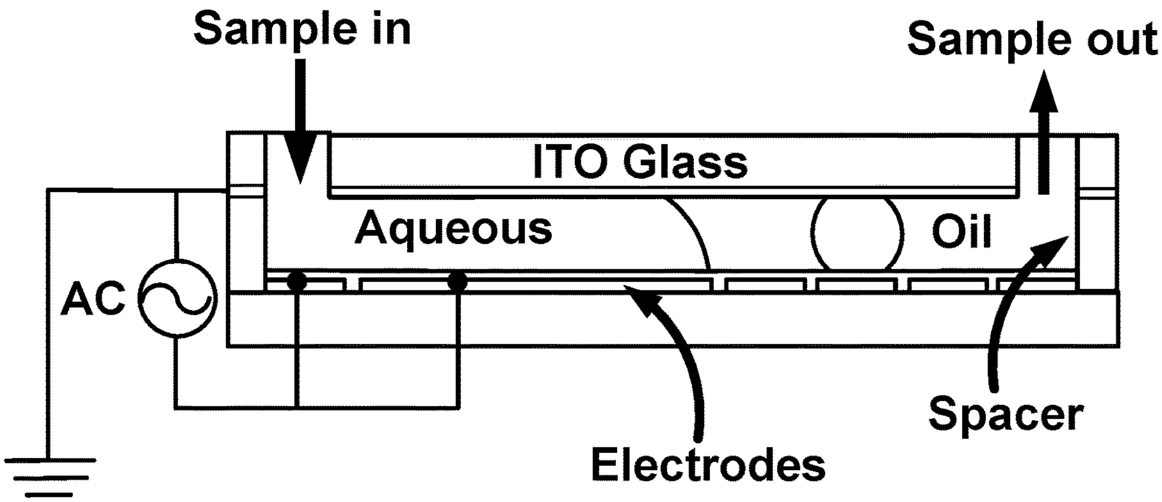

The structure of the DMF device is illustrated in FIGS. 3A, 3B, 7A, and 7B. Overall, the device was composed of a bottom glass substrate patterned with chromium electrodes and an ITO-coated glass substrate as a top plate. The two substrates were connected through double-sided electrically conductive tape and copper tape as the spacer layer (FIG. 7A). The device was pre-filled with OS-30 silicone oil (Dow Corning) prior to loading aqueous samples and was operated at $80V_{RMS}$ at 1 k Hz, while the ITO glass was connected to electrical ground. Fluids were transferred into the device by pipetting through the drilled inlets on the top plate and onto the electrically activated reservoir electrodes (FIG. 7B). To avoid cross-contamination, different samples were introduced onto different reservoir electrodes. Each square electrode in the matrix could hold ~1 μL droplet. The final product was transported to an unused reservoir electrode, and transferred out of the device by pipetting. All supplies and reagents were filtered (0.2 μm), autoclaved or UV-sterilized, except for DNA polymerase and library preparation reagents. All samples and reagents used into the DMF device except library preparation reagents contain a final volume of 0.1% v/v poloxamine detergent Tetronic 90R4 (Octochem) to enhance droplet movement and minimize biofouling (Rackus et al., *Lab on a Chip* 17 (13):2272-2280, 2017; and Leipert and Tholey, *Lab on a Chip* 19 (20):3490-3498, 2019).

Bacterial WGA and Library Preparation in DMF Device

A REPLI-g Single Cell Kit (Qiagen) was used for bacterial WGA. The kit contained DNA denaturing buffer (D2), neutralization buffer, and DNA polymerase. Briefly, 1 μL droplet of bacterial DNA and 1 μL droplet of D2 buffer were mixed in the device and incubated at room temperature for 3 minutes. A 1 μL droplet of neutralization buffer was added to the sample and incubated for 10 minutes to terminate DNA denaturing process. 9 μL of the DNA polymerase was introduced into the device to mix with the sample. The sample was incubated at room temperature for 2 hours, while the electrodes were programmed to turn on and off alternately in a constant manner to agitate the droplets to enhance mixing and thus amplification efficiency. To terminate amplification, the DMF device was taken out of the Dropbot system and incubated at 65° C. on a hotplate for 3 minutes, and was then placed on ice for 1 minute before sliding it back into the Dropbot system. The same procedure was used for amplifying DNA from *C. glutamicum* of different concentrations as well as DNA mixture samples.

A Rapid Sequencing Kit (ONT, SQK-RAD004) was used for library preparation in the DMF device and sequencing using a MinION. Three (3) μL of fragmentation reagent (FRA) were introduced into the device and mixed with the sample. The device was then incubated on a hotplate at 30° C. for 1 minute followed by 80° C. for 1 minute, and was then briefly placed on ice. One (1) μL of rapid adapter (RAP) was added to the sample in the device, and the mixture was incubated at room temperature for 5 minutes. As the aqueous fluid was within ambient silicone oil, evaporation was not observed. The sample was moved to an unused reservoir electrode and transferred out of the device into a 0.2 mL microcentrifuge tube. DNA was quantified using Qubit assay.

Bacterial WGS in MinION Sequencer

A FLO-MIN106D flow cell was primed and the sample prepared for loading according to the manufacturer's instruction. Briefly, 11 μt DNA library, 4.5 μL nuclease-free water, 34 μL sequencing buffer and 25.5 μL loading beads were added into a qPCR tube in a sequential manner and mixed. The final 75 μL sample was immediately loaded into the flow cell sample port in a drop-wise manner to avoid bead aggregation. The sample port, priming port and MinION lid were then closed. The MinION sequencer was controlled by MinKNOW software that performs data acquisition, real-time DNA quality analysis and basecalling. Reads that passed quality filters after basecalling were stored in time-stamped fast5 and fastq files, with 4,000 reads in each of the latter.

Bioinformatics Post-Processing

For Oxford Nanopore reads, adapter sequences were removed from the raw reads using Porechop v0.2.4 (Wick et al., *Microbial Genom* 3 (10), 2017). The fastq files were then concatenated based on their time stamps, and reads mapped using Minimap2 v2.17 (Li, *Bioinformatics* 34 (18):3094-3100, 2018) to a reference genome of *C. glutamicum* ATCC 13032 in NCBI genome database (RefSeq assembly accession GCF_000011325.1). Mapped reads were coordinate-sorted using samtools v1.8 (Li et al., *Bioinformatics* 25 (16):2078-2079, 2009). All processed sequences were visualized in Integrative Genomics Viewer (v.2.8.0) (Robinson et al., *Nature Biotechnol* 29 (1):24-26, 2011). For the profiling of taxonomy, reads with adapter removed were processed using BBDuk entropy filtering from the BBMap tool set v38.69 (Bushnell et al., *PloS One* 12 (10):e0185056, 2017) to mask low complexity regions of the reads. Then, reads were profiled using Centrifuge v1.0.4 (Kim et al., *Genome Res* 26 (12):1721-1729, 2016), using a database based on NCBI RefSeq complete genomes from Bacteria, Archaea and Viruses (as of October 2018), as well as human genome hg38 and mouse genome GRCm38. Taxonomy calls were reported only of their Centrifuge score was larger than 150. The taxonomy pipeline was implemented using Nextflow v19.10.0 (Di Tommaso et al., *Nature Biotechnol* 35 (4):316-319, 2017). As a clarification, Centrifuge was used to test for the presence of amplified DNA from the target organism and to survey putative environmental contaminants in the sample. The database used RefSeq genomes marked as "complete" (as opposed to contigs or scaffolds only) from Bacteria, Archaea and Viruses. The per-read score in Centrifuge is roughly the sum of the square of the k-mer lengths of the matching segments in a read. A threshold of 150 can be interpreted as a matching segment of length 27 bp.

Results and Discussion

In-Tube WGA and Sequencing Quality Control

Figure 8A:
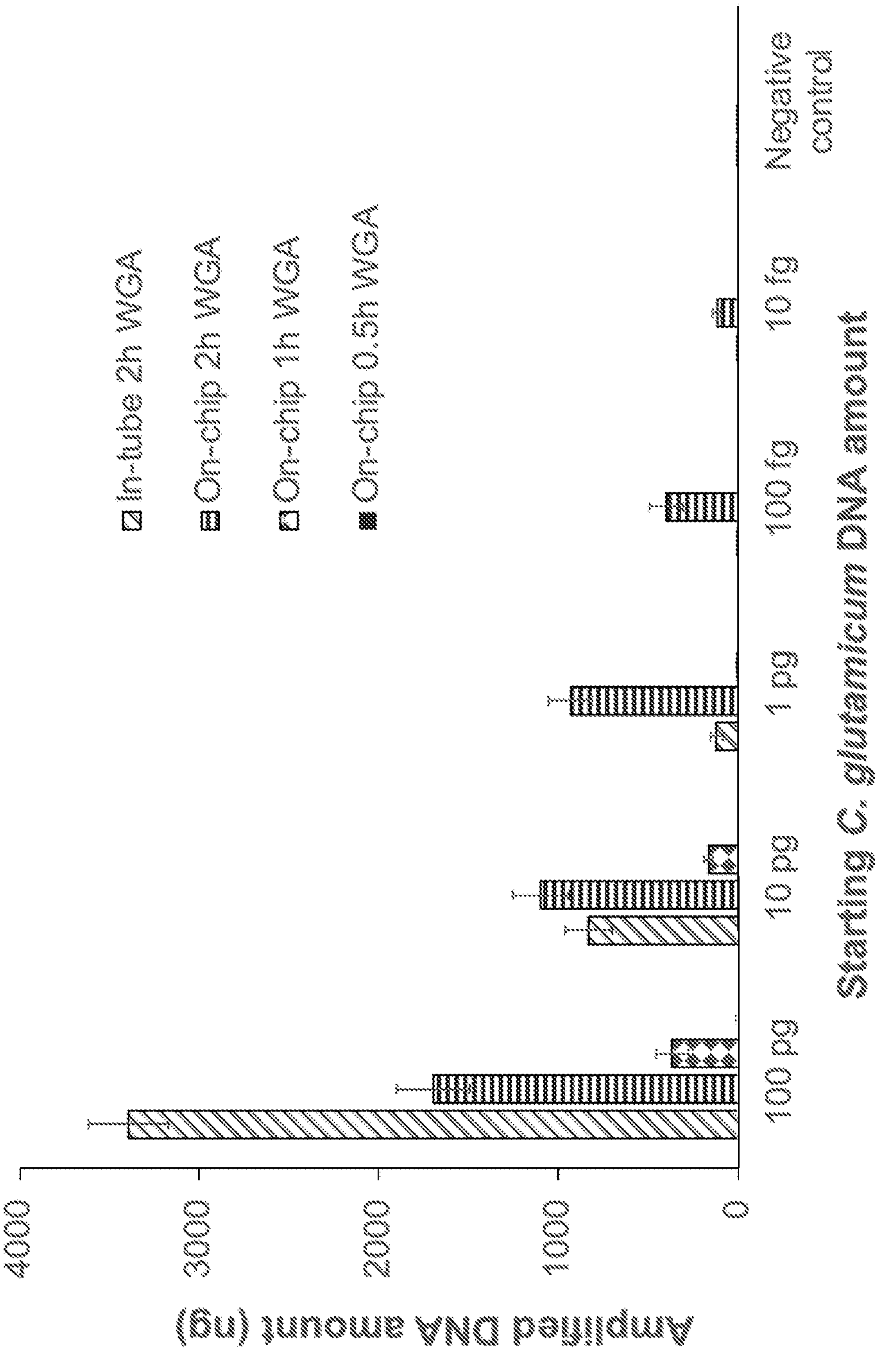
FIGS. 8A-8D show comparisons between the amount of *C. glutamicum* DNA amplified in-tube and on-chip. Each amplification experiment was performed three times, and one replicate was sequenced.
Figure 8B:
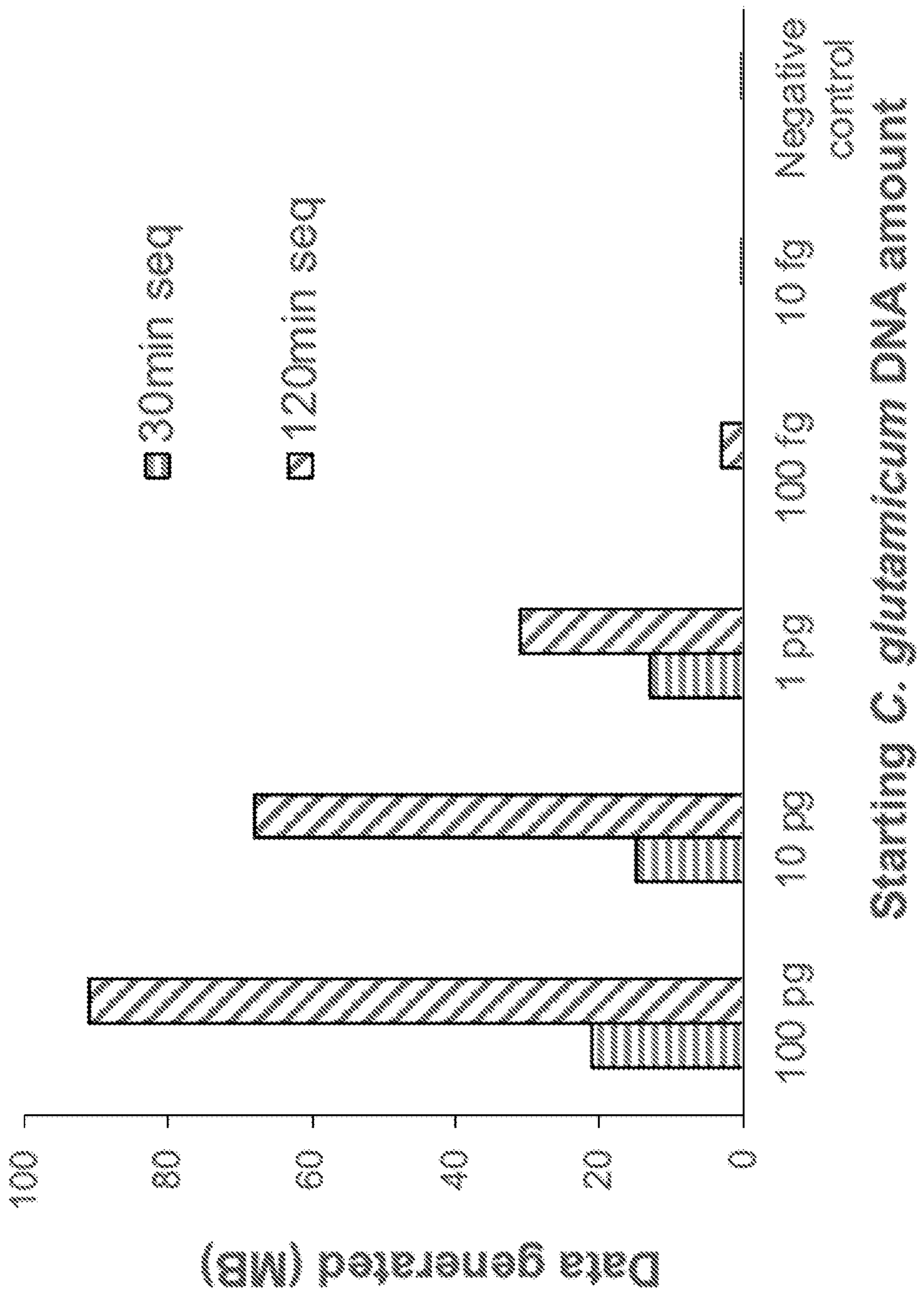
Figure 8C:
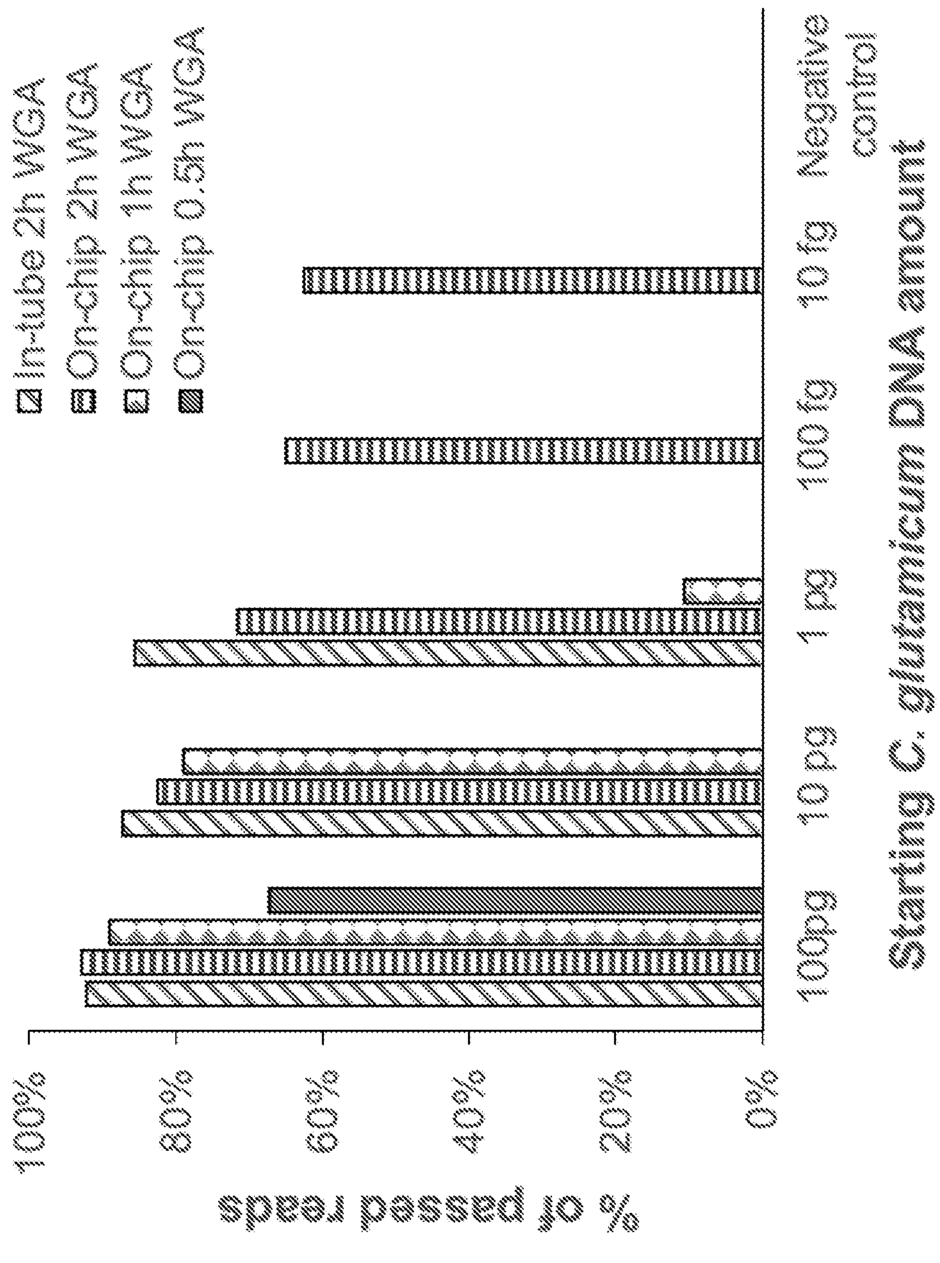

A set of *C. glutamicum* DNA WGA experiments was performed in 0.2 mL microcentrifuge tubes and DMF devices followed by MinION sequencing as a comparative study. Each WGA experiment was repeated 3 times, with one replicate randomly selected from each sample set for sequencing. For in-tube experiments, 2 hours of WGA showed success for samples with 100 pg, 10 pg and 1 pg starting DNA, generating an average of 3.3 μg, 832 ng and 120 ng DNA (FIG. 8A). After a 30 minute sequencing run, >20 Mb data was generated and ready for processing (FIG. 8B). Samples with higher amounts of starting DNA led to larger amounts of DNA available for sequencing after WGA, and thus more data was generated. The amount of DNA obtained between these samples was significantly different from each other ($p<0.005$). During sequencing, DNA sequences with quality score (Qscore)<7.0 were filtered and discarded; over 85% of reads passed quality checks with a medium Qscore of 9.6 (FIG. 8C). The Qscore threshold was the default setting of the basecaller for the MinION sequencing platform. Due to constant advancement in sequencing technology and bioinformatic tools, the basecalling accuracy has continuously improved for the same raw signal. In this work, the per-read nucleotide identity to the reference *C. glutamicum* genome rarely dropped below around 89%.

For samples with 100 fg and 10 fg starting DNA, however, only about 4 ng DNA was generated after 2 hours of WGA, with no data generated with 30 minutes of sequencing. The amount of DNA obtained after amplification was not significantly different between samples or compared with the negative control ($p=0.3$-$0.35$). Extending sequencing time to 120 minutes led to only about 0.2 Mb data output. These results demonstrated that DNA can be sufficiently amplified in-tube for rapid MinION sequencing if the sample contains at least 1 pg starting DNA, but in-tube WGA is not suitable for processing samples with femtograms of starting DNA for rapid sequencing due to the low post-amplification DNA amount.

To test the utility of amplifying femtograms of DNA in-tube for an extended time, 10 fg and 100 fg DNA were amplified for up to 4 hours with three replicates each. For samples with 10 fg starting DNA, only one replicate had a measurement of ~9 ng DNA after amplification, while the other two replicates were below the detection limit of Qubit assay (High Sensitivity). For samples with 100 fg starting DNA, an average of ~11 ng amplified DNA was obtained, but all failed sequencing. These tests showed the advantage of using DMF device for amplifying minute amounts of DNA in a relatively rapid manner.

On-Chip WGA and Sequencing Quality Control

Five different starting amounts of *C. glutamicum* DNA, ranging from 100 pg to 10 fg, were amplified in a DMF device followed by on-chip library preparation and MinION sequencing. Each on-chip WGA was repeated 3 times, with one replicate randomly selected from each sample set for sequencing. After performing WGA in the DMF device for 2 hours, samples with 100 pg were amplified to an average of 1.7 μg DNA (FIG. 8A), significantly higher ($p=0.01$) than the samples with 10 pg and 1 pg starting DNA (~1.1 μg and 933 ng). For samples with 100 fg and 10 fg starting DNA, the average amplified DNA was about 400 ng and about 118 ng, respectively ($p<0.005$).

To test the feasibility of obtaining sufficient DNA within a minimal time, the on-chip WGA experiments were repeated with reduced amplification time (FIG. 8A). For samples with 100 pg and 10 pg starting DNA, the average DNA after 1 hour of amplification was 367 ng and 164 ng, respectively ($p=0.04$); while for the samples with lower starting DNA amounts, amplified DNA was within the range of negative control ($p=0.3$) or below the detection limit of the High Sensitivity Qubit assay. Further reducing on-chip amplification time to 0.5 hour led to only ~7 ng DNA for samples with 100 pg starting DNA, while the DNA amount in the rest of the samples was below the Qubit assay detection limit. Therefore, to obtain the minimum amount of DNA needed for downstream rapid sequencing from as low as 10 fg starting DNA, the minimum time for DNA amplification was determined to be 2 hours. However, the time for DNA amplification can be increased to achieve larger amount of amplified DNA, if necessary.

Figure 8D:
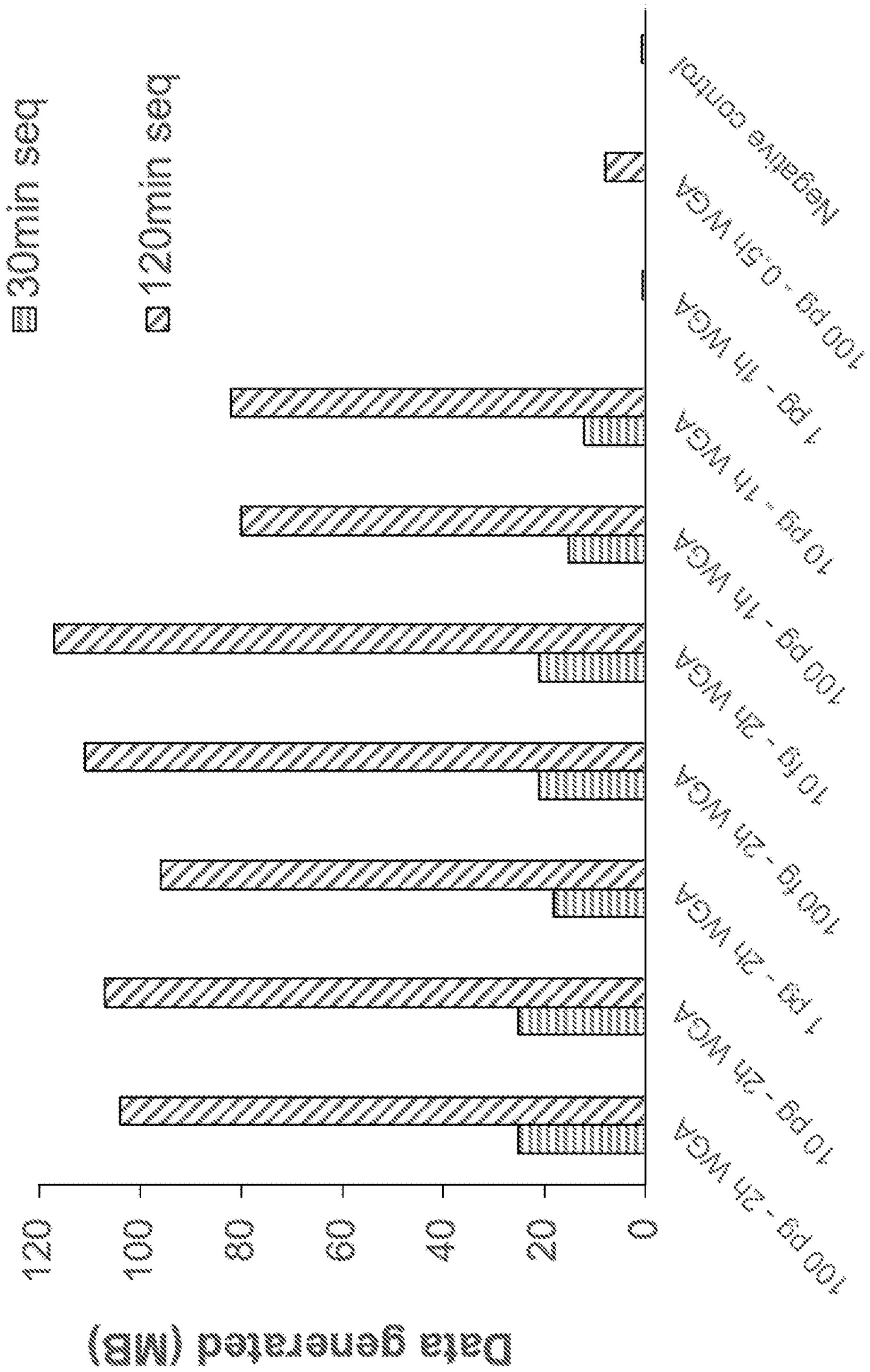

For samples with all five starting DNA amounts amplified on-chip for 2 hours, the first fastq files were generated within 20-30 minutes after sequencing started, with each of the fastq file containing about 20 Mb data (4000 reads) with a medium Qscore of 9.5; 65-90% sequenced reads passed quality check (FIGS. 8C and 8D). These generated fastq files were immediately sent to the taxonomy calling pipeline to identify the bacterial species, which takes about 10 minutes. Extending sequencing to 2 hours generated multiple fastq files that were concatenated and processed in the same manner. As a comparison, samples amplified for 1 hour and 0.5 hour on-chip with a detectable range of DNA were also sequenced (FIGS. 8C and 8D). These samples had low amounts of DNA and insufficient high-quality DNA; the percentage of sequencing reads passing quality check was low and required extended sequencing time to obtain minimal data (~0.5 Mb). Since the aim of this work was to achieve bacterial identification with 30 minutes of sequencing in a reliable manner, samples amplified on-chip that were below the detection limit of Qubit assay were not sequenced.

Contamination profile in MinION sequencing

Figure 9A:
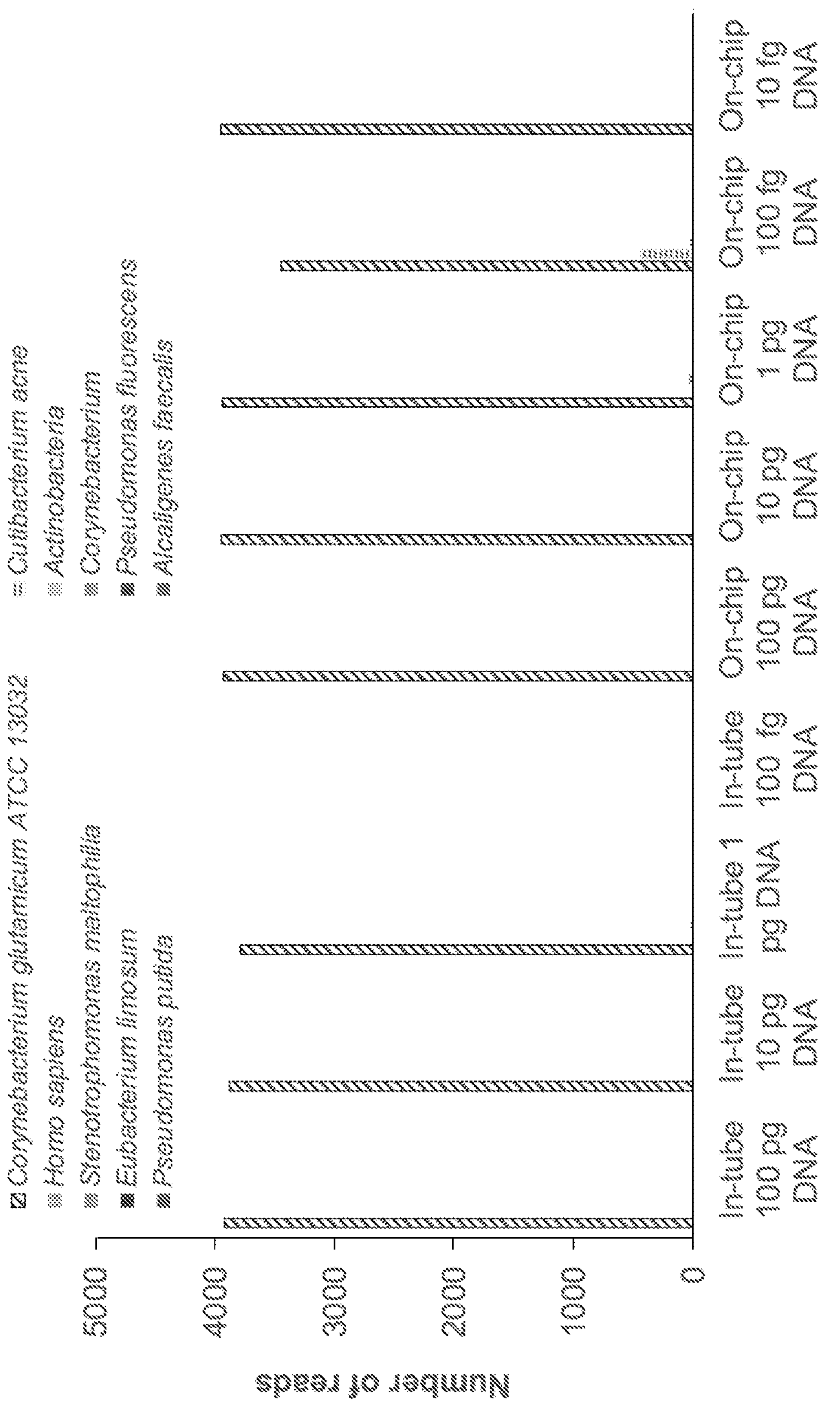
FIGS. 9A and 9B show contamination profiles for sequenced samples.
Figure 9B:
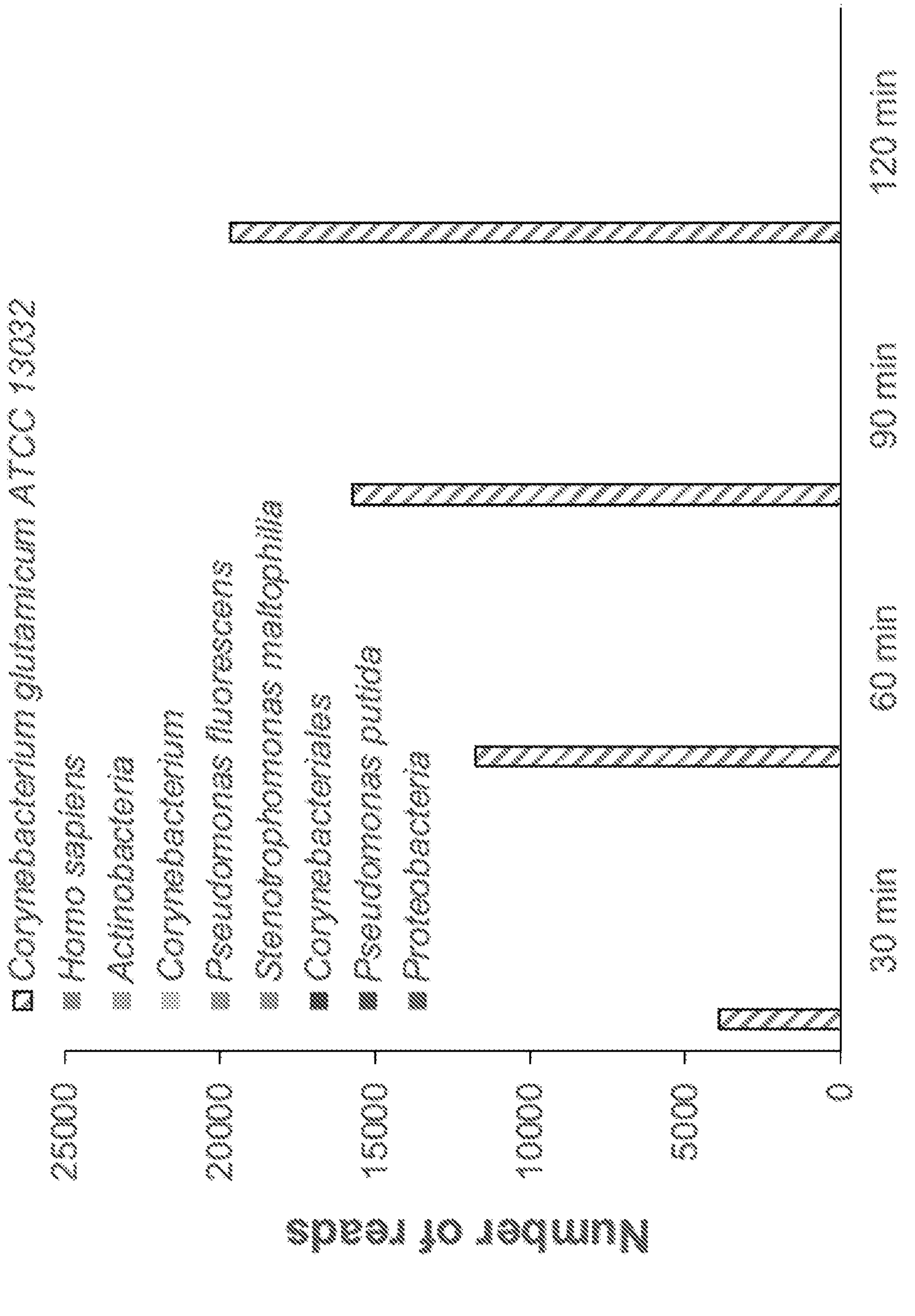

Contaminants detected by MinION sequencing are shown in FIGS. 9A and 9B. For the 100 pg *C. glutamicum* DNA amplified on-chip, the target species was reliably detected after 30 minutes of sequencing, with 3900 *C. glutamicum* reads and <10 contaminant reads. Extending the sequencing time led to a higher number of *C. glutamicum* reads, with the number of reads doubling every 30 minutes. 120 minutes of sequencing generated about 5 times more *C. glutamicum* reads than 30 minutes of sequencing; the number of reads of the contaminants also increased by about 5 times but still remained low overall (<50 reads) (FIG. 9A). FIG. 9B shows the contamination profile within 30 minutes of sequencing for samples with different amount of starting DNA amplified for 2 hours on-chip and in-tube. Despite the contaminants present in the samples sequenced, the target species displayed at least 10× higher number of reads.

Possible contaminating sources include the original culture, reagent and airborne contaminants, human-related contamination, and equipment sources. *Homo sapiens* is reported as an expected contamination in whole genome amplification (Hammond et al., *Microbiome* 4 (1):52, 2016). Contamination can be introduced at any stage of the process, including initial cell cultivation, handling, experimentation, sample transfer, library preparation, and sequencing. Among the reads of the contaminants, *Cutibacterium acnes* reads appeared higher than other contaminants; this species is commonly found on human skin (Lewin et al., Ann Rev Microbiol 70:235-254, 2016; and Platsidaki and Dessinioti, *F*1000Research 7, 2018). A low percentage of contaminant reads appeared as *Corynebacterium*. This is likely due to the low quality of some *C. glutamicum* reads that could not be called beyond genus level, and therefore were not assigned to the target species. To investigate the level of contamination of reagents, negative control samples (sterile PBS) amplified in-tube and on-chip for 2 hours were sequenced. *C. glutamicum* and *E. coli* lambda virus DNA was detected in these negative control samples, but at a low amount. To investigate if the cross-contamination stemmed from the original DNA samples, direct sequencing was performed on the extracted *C. glutamicum* DNA, *P. somerae* DNA, and *E. coli* lambda DNA, respectively, without amplification. The results showed that there was no cross-contamination of any of the three species in the original samples.

Coverage of MinION Sequenced Reads

Figure 10:
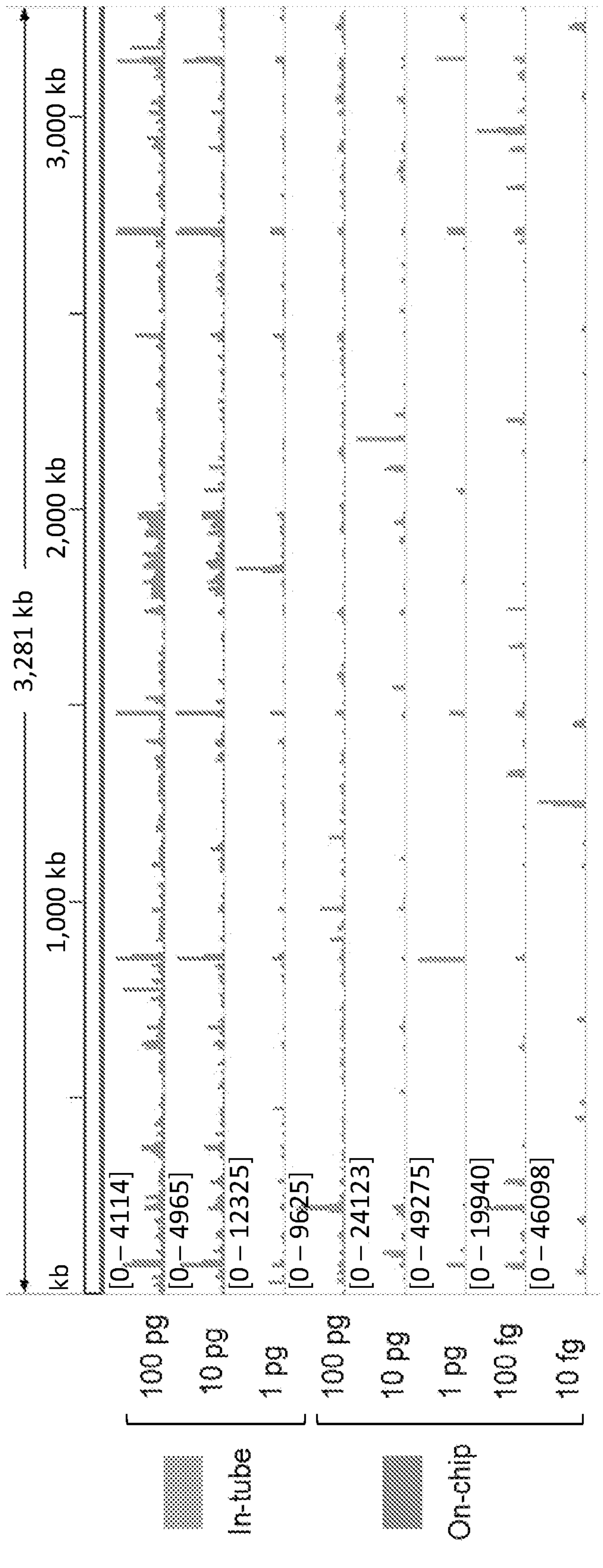
FIG. 10 is a graph plotting the coverage of sequencing reads processed and mapped to the *C. glutamicum* reference genome, from samples amplified for 2 hours.

Raw reads were mapped to the reference genome of *C. glutamicum* ATCC 13032 after adapters were removed (FIG. 10). As a general trend, samples with higher starting DNA amounts showed more genome coverage after 30 minutes of sequencing (Table 3). For samples with picograms of starting DNA, those that were amplified in-tube showed more complete genome coverage than those amplified on-chip. However, for samples with femtograms of starting DNA, not enough DNA was obtained for rapid MinION sequencing with in-tube amplification. Therefore, to obtain sufficient DNA from samples with low DNA amounts in a rapid manner, it is essential to enhance amplification efficiency by implementing constant mixing strategies. For samples amplified on-chip, higher amounts of starting DNA led to increased genome coverage. About 76.7% genome coverage was achieved for the sample with 100 pg starting DNA, but genome coverage decreased as the amount of starting DNA decreased. It is noted that three replicates were sequenced for samples with femtograms of starting DNA, as this is the range that DMF-based amplification is advantageous over in-tube amplification.

TABLE 3

Genome coverage of *C. glutamicum* DNA after 30 minute sequencing in MinION

| | 100 pg | 10 pg | 1 pg | 100 fg | 10 fg |
|---|---|---|---|---|---|
| In-tube | 74.5% | 58.6% | 50.0% | N/A | N/A |
| On-chip | 76.8% | 43.6% | 16.9% | 18.6% (±1.5%) | 10.5% (±5.0%) |

Despite the relatively low genome coverage for samples with as low as 10 fg starting DNA (equivalent to the amount of DNA within a single bacterial cell), the genome sequence was unique enough to identify the bacterial strain. Individual reads also can be taxonomically assigned, furthering the certainty of the call. However, the accuracy can vary for different microbial species, depending on the extent of their representation in genomic databases. Taken into consideration hands-on time, including flow cell priming, sample loading and running the sequencing data through the taxonomy calling pipeline, it was feasible to keep sample-to-answer time within 3 hours. Such a rapid turnaround time for bacterial identification is especially essential in urgent medical situations involving bacterial infections such as Sepsis, as timely diagnosis can lead to effective and targeted treatment in a prompt manner. It is noted that in some cases, a lysis buffer effective for lysing single bacterial cells for microfluidic-based whole genome amplification is used, including buffers adapted from those described elsewhere (see, e.g., Liu et al., *Micromachines* 9 (8):367, 2018). Such a buffer can provide the ability to effectively lyse low-abundance bacterial cells without compromising DNA quality.

Rapid WGA and Sequencing of Multiple Bacterial Species

Figure 11A:
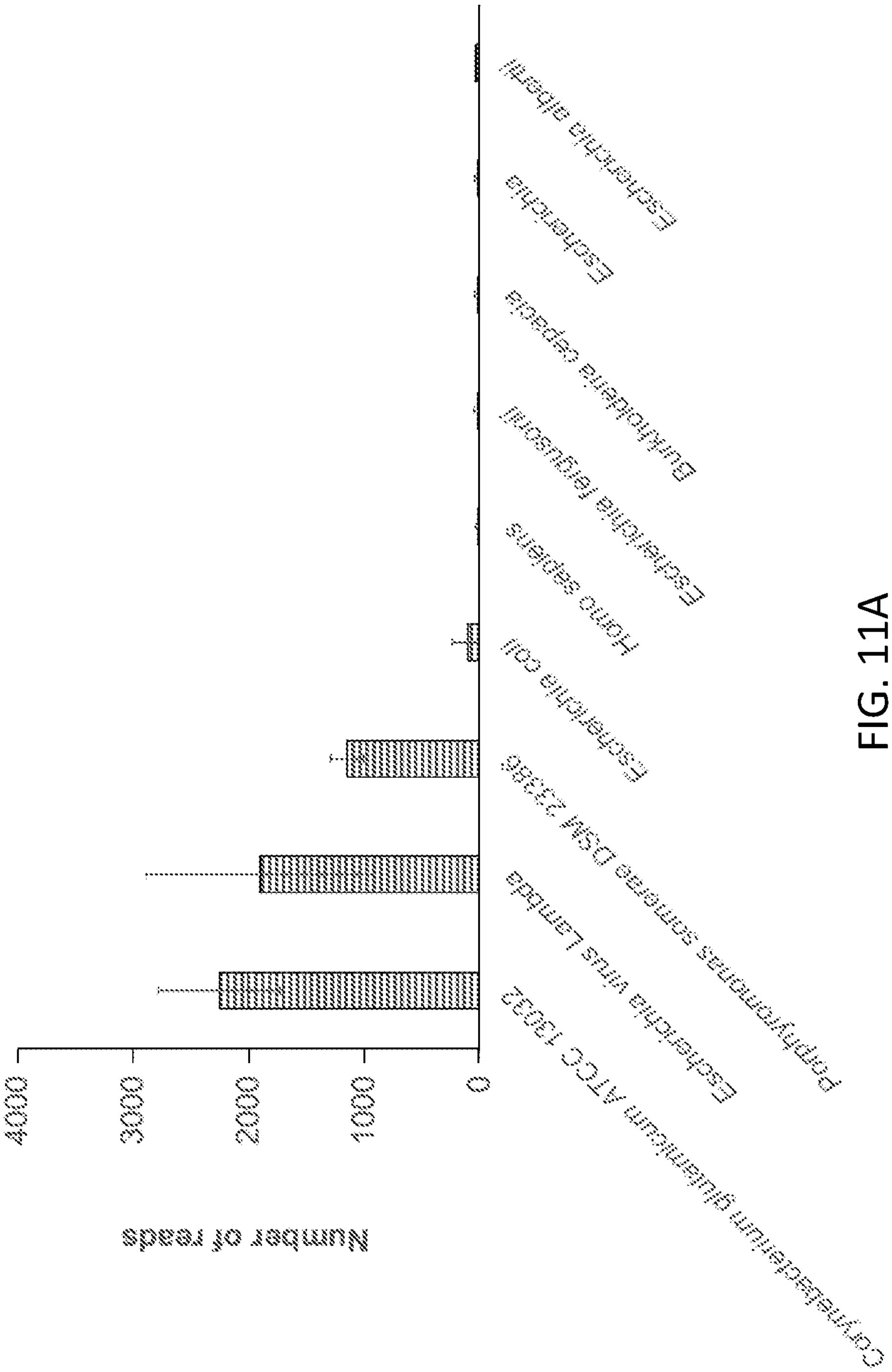
FIGS. 11A-11D are graphs plotting sequencing results of on-chip amplified samples with different initial amounts of *C. glutamicum, P. somerae*, and *E. coli* bacteriophage lambda DNA. Three amplification tests and sequencing were performed on each sample. Initial amounts used were: 100 fg lambda, 100 fg *C. glutamicum*, and 50 fg *P. somerae* DNA (FIG. 11A); 10 fg lambda, 10 fg *C. glutamicum*, and 50 fg *P. somerae* DNA (FIG. 11B); 10 fg lambda, 20 fg *C. glutamicum*, and 100 fg *P. somerae* DNA (FIG. 11C), and 1 pg lambda, 50 fg *C. glutamicum*, and 10 fg *P. somerae* DNA (FIG. 11D).
Figure 11B:
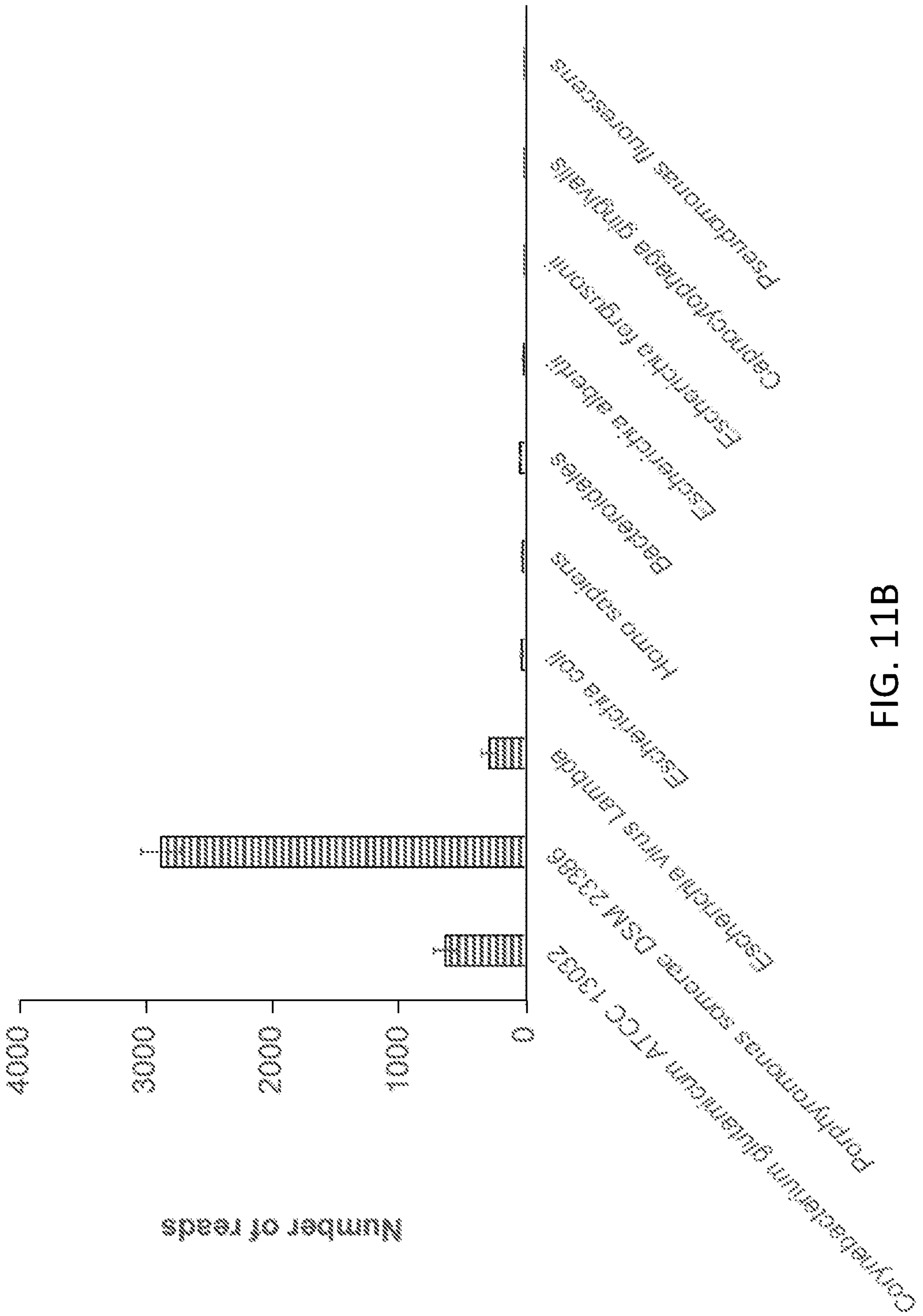
Figure 11C:
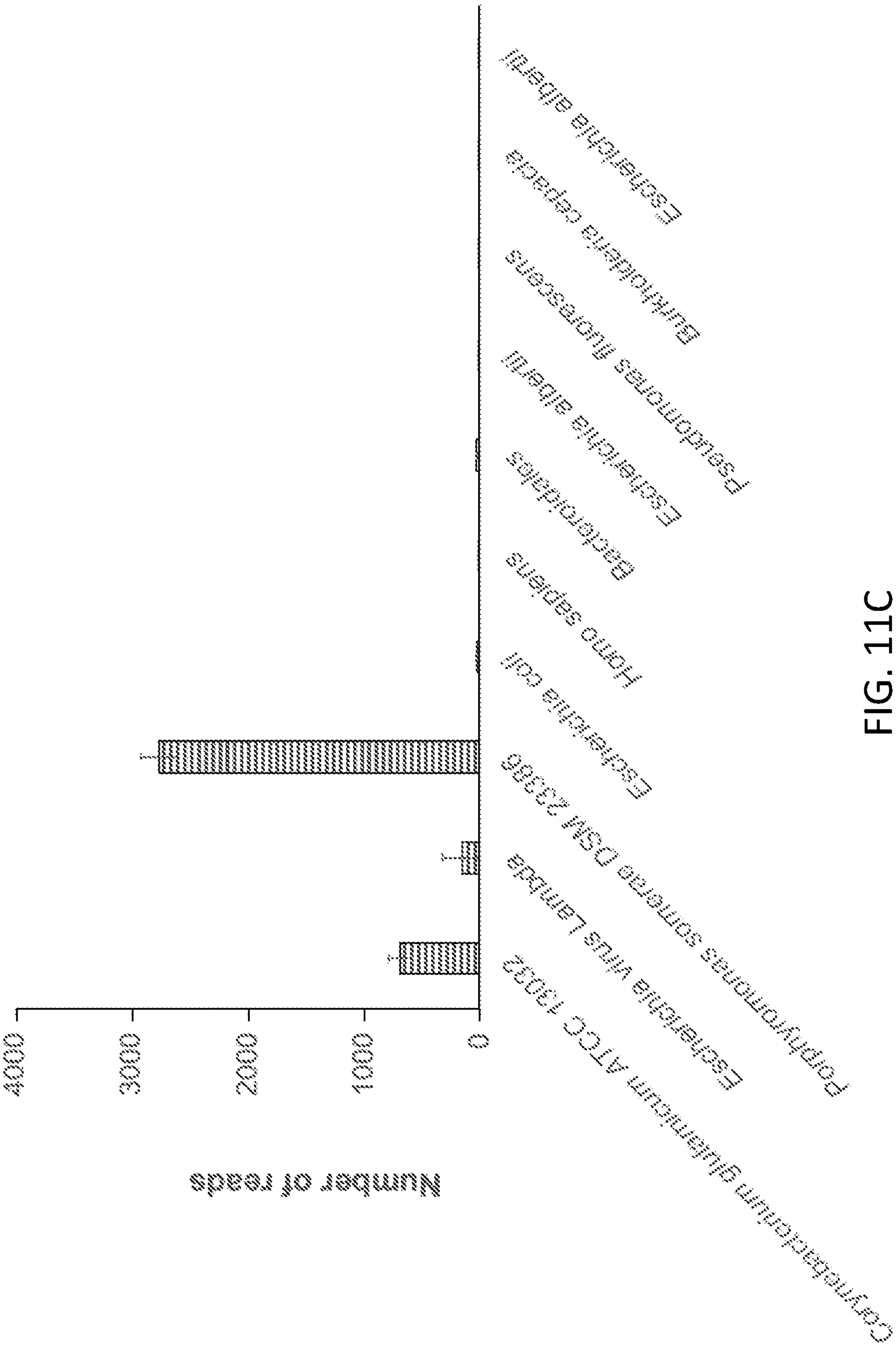
Figure 11D:
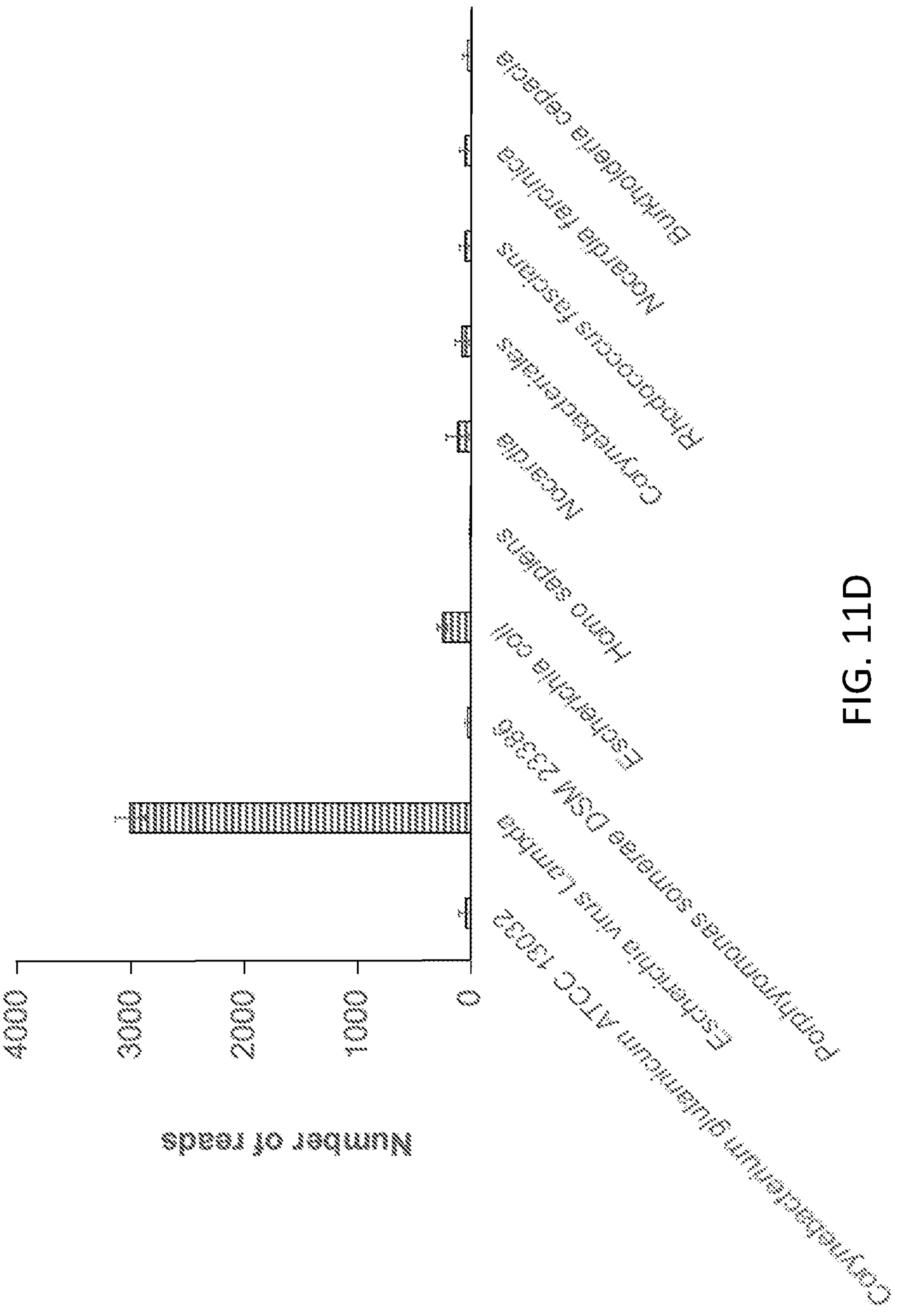

The method described herein was tested for its ability to detect multiple bacterial species. In these experiments, samples with *C. glutamicum* DNA, *P. somerae* DNA, and *E. coli* bacteriophage lambda DNA were used, with starting DNA amounts ranging from 1 pg to 10 fg in randomly generated combinations. As indicated in FIGS. 11A-11C, it was possible to detect all three species if the amount of starting DNA between these species did not differ by more than 10×. In these cases, the number of reads for all three species was more than 8-fold higher than the number of contaminating reads, therefore reliably detecting the presence of these species within the samples. However, when the initial amount of *E. coli* bacteriophage lambda DNA exceeded the amounts of *C. glutamicum* DNA and *P. somerae* DNA by more than 20-fold, the number of reads of *C. glutamicum* and *P. somerae* fell within the range of contaminating reads and thus remained undetected (FIG. 11D).

To determine whether low-abundance bacterial cells could be effectively lysed without compromising DNA quality, 1 μL of cultured *C. glutamicum* cells at a concentration of $10^3$ cells/mL was tested in the device, following a protocol for amplifying purified DNA. Amplified products were below the detection limit of High Sensitivity Qubit assay, possibly due to lack of lysis. To improve the efficiency of bacterial lysis, cells were incubated for 15 minutes at 37° C. in a custom lysis buffer (Liu et al., supra) containing 100 mM DTT and 200 U/μL lysozyme. Results showed amplification of *C. glutamicum* cells at a single cell level, with the number of sequenced reads showing larger variability between amplification tests compared with amplified purified DNA (FIG. 7A), perhaps due to cell-to-cell variability of *C. glutamicum* lysis. Nevertheless, the number of *C. glutamicum* reads was ~100-fold higher than contaminant reads, from which they were easily distinguished.

Figure 12:
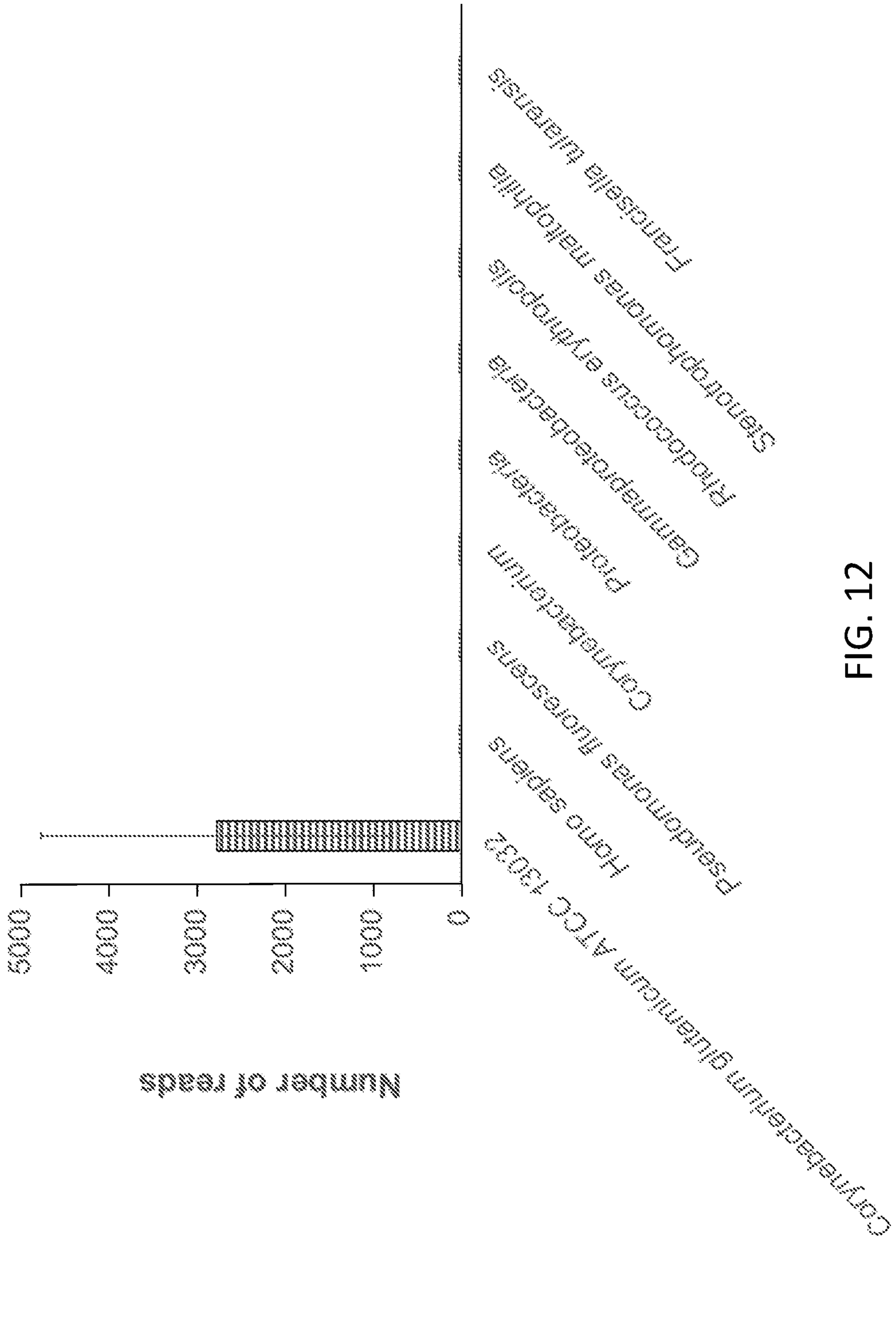
FIG. 12 is a graph plotting the number of reads for a single *C. glutamicum* cell that was lysed and amplified on a chip, demonstrating the feasibility of effective bacterial cell lysis followed by amplification on a single cell level.

To investigate the possibility of rapid detection of bacteria in the presence of human cells, samples of cultured *C. glutamicum* were tested alone or mixed with human KLE cells. No *C. glutamicum* sequencing reads were detected when the two were mixed at a 100:1 ratio for amplification, but when the ratio of *C. glutamicum* to KLE cells was increased to 500:1, about 30 *C. glutamicum* sequencing reads were detected (about 100 times lower than the number of *Homo sapiens* reads; FIG. 12). To enable detection of bacterial cells in clinical samples, as many human cells as possible should be removed prior to amplification and sequencing. This can be achieved using strategies such as dielectrophoretic separation (Chen et al., *Micromachines* 11(7):700, 2020; and Zhang et al., *Micromachines* 10(6): 423, 2019), deterministic lateral displacement (Hochstetter et al., *ACS nano* 14(9):10784-10795, 2020; and McGrath et al., *Lab on a Chip* 14(21):4139-4158, 2014), and/or microfiltration (Shields et al., *Lab on a Chip* 15(5):1230-1249, 2015) into microfluidic platforms. At the current stage, we focused on rapid amplification of minute amounts of bacterial DNA with minimal contamination. Future efforts will be centered on whole genome amplification of low-abundance bacterial cells and integration of the aforementioned human cell depletion into the to improve sensitivity and potential clinical applications.

Taken together, the studies described herein utilized novel technologies including palm-sized DMF devices and MinION sequencer to support a 2 hour amplification of as little as 10 fg bacterial DNA (equivalent to the amount of DNA in a single bacterial cell) with high purity, yielding bacterial species identity with 30 minutes of sequencing. This approach also showed success in identifying bacterial species within samples with multiple bacteria in a rapid manner. Thus, bacterial species were identified using WGS from samples harboring femtograms of DNA within 3 hours, with minimal contamination.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A microfluidics device comprising:

a first substrate comprising a planar surface that comprises a first location, a second location, a third location, and an array of chromium electrodes defining microfluidic channels on the first substrate, the array of chromium electrodes comprising one or more reservoir electrodes at the second location and one or more reservoir electrodes at the third location, wherein the chromium electrodes are positioned between the first location and the second location and between the second location and the third location, and wherein the array of chromium electrodes are configured to move a biological sample of a mammal from said first location to said second location and from said second location to said third location; and a second substrate comprising an indium tin oxide (ITO) coating, the second substrate positioned over the first substrate, wherein the first substrate and the second substrate comprise glass and are separated by a spacer layer, wherein the second substrate defines one or more inlets configured to receive one or more droplets comprising the biological sample, the reagents for performing WGA, and the reagents for performing library construction, and wherein the second substrate is configured to be electrically grounded, wherein said first location comprises one or more immobilized antibodies and is configured to capture target cells of said mammal from said biological sample via said one or more immobilized antibodies to form a cell-free sample having a reduced number of the target cells that were present in said biological sample, wherein said second location comprises the one or more reservoir electrodes at the second location, wherein the one or more reservoir electrodes at the second location are configured to receive, through the one or more inlets, one or more droplets comprising reagents for performing whole genome amplification (WGA), wherein said reagents for performing WGA comprise a DNA polymerase, a DNA denaturing buffer, and a neutralization buffer, and wherein the array of chromium electrodes is configured to move the cell-free sample to the one or more reservoir electrodes at the second location and mix the cell-free sample with the one or more droplets comprising the reagents for performing WGA to form an amplified sample, and wherein said third location comprises the one or more reservoir electrodes at the third location, wherein the one or more reservoir electrodes at the third location are configured to receive, through the one or more inlets, one or more droplets comprising reagents for performing library construction, wherein said reagents for performing library construction comprise a fragmentation reagent and an adapter, and wherein the array of chromium electrodes is configured to move the amplified sample to the one or more reservoir electrodes at the third location and mix the amplified sample with the one or more droplets comprising the reagents for performing library construction to form a sequencing ready sample.

2. The device of claim 1, wherein the device is a digital microfluidic chip.

3. The device of claim 1, wherein the biological sample comprises blood.

4. The device of claim 1, wherein the one or more immobilized antibodies comprise an anti-CD45 antibody.

5. The device of claim 1, wherein the target cells of said mammal from said biological sample comprise white blood cells, red blood cells, platelets, or combinations thereof.

6. The device of claim 1, wherein the one or more antibodies are configured to bind from about 1,000 to about 100,000 of said target cells of said mammal from said biological sample per droplet of the biological sample.

7. The device of claim 1, wherein the array of chromium electrodes comprise a coating disposed thereon.

8. The device of claim 7, wherein the coating comprises an insulative material, a hydrophobic material, or an insulative hydrophobic material.

9. The device of claim 1, wherein the device is further configured to transfer the sequencing ready sample.

* * * * *